(12) United States Patent
Harris et al.

(10) Patent No.: US 9,012,471 B2
(45) Date of Patent: Apr. 21, 2015

(54) GLUCOSE METABOLISM MODULATING COMPOUNDS

(75) Inventors: Paul Harris, New York, NY (US);
Antonella Maffei, New York, NY (US);
Yuli Xie, Shanghai (CN); Donald Landry, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 738 days.

(21) Appl. No.: 12/937,177

(22) PCT Filed: Apr. 10, 2009

(86) PCT No.: PCT/US2009/002246
§ 371 (c)(1),
(2), (4) Date: Jan. 31, 2011

(87) PCT Pub. No.: WO2009/126305
PCT Pub. Date: Oct. 15, 2009

(65) Prior Publication Data
US 2011/0118300 A1    May 19, 2011

Related U.S. Application Data

(60) Provisional application No. 61/123,785, filed on Apr. 11, 2008.

(51) Int. Cl.
*A61K 31/4375* (2006.01)
*C07D 455/06* (2006.01)
*C07D 211/86* (2006.01)

(52) U.S. Cl.
CPC .................................. *C07D 211/86* (2013.01)

(58) Field of Classification Search
USPC .......................................... 546/296; 514/317
See application file for complete search history.

(56) References Cited

U.S. PATENT DOCUMENTS

| | | | |
|---|---|---|---|
| 5,231,181 A | 7/1993 | Dyson et al. | |
| 5,936,128 A | 8/1999 | Ellsworth et al. | |
| 6,649,604 B2 | 11/2003 | Spohr et al. | |
| 2010/0204258 A1 | 8/2010 | Harris et al. | |
| 2011/0294800 A1 | 12/2011 | Xie et al. | |

FOREIGN PATENT DOCUMENTS

| WO | WO 2006/091697 | 8/2006 |
|---|---|---|
| WO | 2008/112278 | 9/2008 |

OTHER PUBLICATIONS

Franklin Davis et al Alkaloid Synthesis, 2000.*
Xie Y et al, 2008, Novel Hypoglycemics, dihydropyridones serendipitously discovered from O- versus C-alkylation in the synthesis of VMAT2 antagonists.*
Raffo et al., Role of vasicular monoamine transporter type 2 in rodent insulin secretion and glucose metabolism revealed by its specific antagonist tetrabenazine, Journal of Endocrinology, 196, pp. 41-49 (2008).
Sagne et al., The Photoactivatable Inhibitor 7-Azido-8-iodoketanserin Labels the N Terminus of the Vesicular Monoamine Transporter from Bovine Chromaffin Granules, Biochemistry, 36, pp. 3345-3352 (1997).
Lundquist I, "Insulin secretion. Its regulation by monoamines and acid amyloglucosidase," Acta Physiol Scand Suppl 372:1-47 (1971).
Lundquist I et al., "Monoamines in pancreatic islets of guinea pig, hamster, rat, and mouse determined by high performance liquid chromatography," Pancreas 4:662-667 (1989).
Maffei A et al., "Identification of tissue-restricted transcripts in human islets," Endocrinology 145:4513-4521 (2004).
Mahony C et al., "Species variation in pancreatic islet monoamine uptake and action," Diabetes 26:257-261 (1977).
Murthy R et al., "Whole body [11C]-dihydrotetrabenazine imaging of baboons: biodistribution and human radiation dosimetry estimates", Eur J Nucl Med Mol Imaging, 2008, 35, 790-797.
Natalucci S et al., "Age-related analysis of glucose metabolism in spontaneously hypertensive and normotensive rats," Exp Physiol 88:399-404 (2003).
Nogueira CR, "Modulation of insulin secretion and 45Ca2+ efflux by dopamine in glucose-stimulated pancreatic islets," Gen Pharmacol 25:909-916 (1994).
Non-Final Office Action mailed Nov. 21, 2013 in U.S. Appl. No. 13/058,142 (Paper No. 20131118).
Pettibone DJ, "Tetrabenazine-induced depletion of brain monoamines: characterization and interaction with selected antidepressants," Eur J Pharmacol 102:425-430 (1984).
Quinn GP et al., "Biochemical and pharmacological studies of RO 1-9569 (tetrabenazine), a nonindole tranquilizing agent with reserpine-like effects," J Pharmacol Exp Ther 127:103-109 (1959).
Response to Non-Final Office Action mailed May 20, 2014 in U.S. Appl. No. 13/058,142.
Rosati G et al., "Effects of long-term L-dopa therapy on carbohydrate metabolism in patients with Parkinson's disease," European Neurology 14:229-239 (1976).
Rubi B et al., "Dopamine D2-like receptors are expressed in pancreatic beta cells and mediate inhibition of insulin secretion," J Biol Chem 280:36824-36832 (2005).
Scherman D, "Dihydrotetrabenazine binding and monoamine uptake in mouse brain regions," J Neurochem 47:331-339 (1986).
Scherman D et al., "Acido-basic properties of the catecholamine uptake inhibitors tetrabenazine and dihydrotetrabenazine," Biochimie 64:915-921 (1982).
Scherman D et al., "Characterization of the monoamine carrier of chromaffin granule membrane by binding of [2-3H]dihydrotetrabenazine," Proc Natl Acad Sci USA 80:584-588 (1983).
Scherman D et al., "Reserpine binding to bovine chromaffin granule membranes. Characterization and comparison with dihydrotetrabenazine binding," Mol Pharmacol 25:113122 (1984).
Shankar E et al., "Dopaminergic regulation of glucose-induced insulin secretion through dopamine 02 receptors in the pancreatic islets in vitro," IUBMB Life 58:157-163 (2006).

(Continued)

*Primary Examiner* — Rita Desai
(74) *Attorney, Agent, or Firm* — Bryan Cave LLP

(57) ABSTRACT

The present invention provides, inter alia, dihydropyridone compounds and compositions, including analogs of a vesicular monoamine transporter type 2 (VMAT2) antagonist. The present invention also provides methods of using such compounds/analogs for modulating glucose levels, and/or preventing, treating, or ameliorating the effects of diabetes and hyper-glycemia.

12 Claims, 13 Drawing Sheets

(56) References Cited

OTHER PUBLICATIONS

Shapiro A.M.J. et al., "Islet preparation in seven patients with type I diabetes mellitus using a glucocortoid-free immunosuppressive regimen", New England Journal of Medicine, 2000, 343(4), 230-238.
Sharp GW, "Mechanisms of inhibition of insulin release," Am J Physiol 271: C1781-1799 (1996).
Souza F et al., "Current progress in non-invasive imaging of beta cell mass of the endocrine pancreas," Curr Med Chem 13:2761-2773 (2006).
Souza F. et al., "Longitudinal noninvasive PET-based β cell mass estimates in a spontaneous diabetes rat model", J Clin Invest., 2006, 116(6), 1506-1513.
Squires PE et al., "Co-ordinated Ca(2+)-signalling within pancreatic islets: does beta-cell entrainment require a secreted messenger," Cell Calcium 31:209-219 (2002).
Storto M et al., "Insulin secretion is controlled by mGlu5 metabotropic glutamate receptors," Mol Pharmacol 69:1234-1241 (2006).
Taylor AW, "Free fatty acid levels in exercised and nonexercised reserpinized rats," Am J Physiol 223:319-322 (1972).
Uehara S et al., "Metabotropic glutamate receptor type 4 is involved in autoinhibitory cascade for glucagon secretion by alpha-cells of islet of Langerhans," Diabetes 53:998-1006 (2004).
Varoqui H et al., "Vesicular neurotransmitter transporters. Potential sites for the regulation of synaptic function," Mol Neurobiol 15:165-191 (1997).
Wang Y et al., "Glucagon-like peptide-1 can reverse the age-related decline in glucose tolerance in rats," J Clin Invest 99:2883-2889 (1997).
Watanabe T et al., "Immunohistochemical colocalization of insulin, aromatic L-amino acid decarboxylase and dopamine beta-hydroxylase in islet B cells of chicken pancreas," Cell Tissue Res 263:131-136 (1991).
Weksler-Zangen S et al., "The newly inbred cohen diabetic rat: a nonobese normolipidemic genetic model of diet-induced type 2 diabetes expressing sex differences," Diabetes 50:2521-2529 (2001).
Wilson JP et al., "Beta cell monoamines: further evidence for their role in modulating insulin secretion," Am J Physiol 227:305-312 (1974).
Xie Y, et al., "Novel hypoglycemic dihydropyridones serendipitously discovered from O- versus C-alkylation in the synthesis of VMAT2 antagonist," Bioorg. Med. Chem. Lett., 5111-5114 (2008).
Yamada H, et al., "Ca2+-dependent exocytosis of L-glutamate by alphaTC6, clonal mouse pancreatic alpha-cells," Diabetes 50: 1012-1020 (2001).
Zern RT et al., "Effect of increased pancreatic islet norepinephrine, dopamine and serotonin concentration on insulin secretion in the golden hamster" Diabetologia 18:341-346 (1980).
Zheng G et al., "Vesicular Monoamine Transporter 2: Role as a Novel Target for Drug Development", AAPS J., 8(4), E682-692, (2006).
Adeghate E et al., "Distribution of acetylcholinesterase- and monoamine oxidase-positive neurons in pancreatic tissue transplant," Acta Histochem 89: 183-186 (1990).
Adeghate E et al., "Dopamine-beta-hydroxylase-positive nerves in normal and transplanted pancreatic tissue in the anterior eye-chamber of rats," J Chem Neuroanat 4:223-227 (1991).
AFT Pharmaceuticals. Datasheet Xenazine 25. [online] Available on the internet at <<http://www.medsafe.govt.nz/profs/datasheet/x/Xenazine25tab.pdf>> Prepared on Sep. 12, 2006 [retrieved on Mar. 29, 2012].
Ahrén B, "Autonomic regulation of islet hormone secretion—implications for health and disease," Diabetologia 43:393-410 (2000).
Ahrén B et al., Neuropeptidergic versus cholinergic and adrenergic regulation of islet hormone secretion. Diabetologia 29:827-836 (1986).
Ahrén B et al,, "Effects of L-dopa-induced dopamine accumulation on 45Ca2+ efflux and insulin secretion in isolated rat islets," Pharmacology 30:71-82 (1985).

Ahrén B et al,, "Influence of the sympatho-adrenal system and somatostatin on the secretion of insulin in the rat," J Physiol 312:563-575 (1981).
Aleyassine H et al., "Dual action of antidepressant drugs (MAO inhibitors) on insulin release," Endocrinology 96:702-710 (1975).
Anlauf M. et al., "Expression of the Two Isoforms of the Vesicular Monoamine Transporter (VMAT1 and VMAT2) in the Endocrine Pancreas and Pancreatic Endocrine Tumors", J Histochem Cytochem., 2003, 51(8), 1027-1040.
Arneric SP et al., "Dopamine analog-induced hyperglycemia in rats: involvement of the adrenal medulla and the endocrine pancreas," J Pharmacol Exp Ther 228:551-559 (1984).
Arneric SP et al., "Inhibition of insulin release from rat pancreatic islets by drugs that are analogues of dopamine," Diabetes 33:888-893 (1984).
Barker CJ et al., "Phosphorylated inositol compounds in beta-cell stimulus-response coupling," Am J Physiol Endocrinol Metab 283:E1113-1122 (2002).
Bird JL et al., "Pancreatic islets: a tissue rich in serotonin," Diabetes 29:304-308 (1980).
Borelli MI et al., "Possible modulatory effect of endogenous islet catecholamines on insulin secretion," BMC Endocr Disord 1:1 (2001).
Borelli MI et al., "Presence of DOPA decarboxylase and its localisation in adult rat pancreatic islet cells," Diabetes Metab 23:161-163 (1997).
Borelli MI et al., "Tyrosine hydroxylase activity in the endocrine pancreas: changes induced by short-term dietary manipulation," BMC Endocr Disord 3:2 (2003).
Brice NL et al., "Metabotropic glutamate and GABA(B) receptors contribute to the modulation of glucose-stimulated insulin secretion in pancreatic beta cells," Diabetologia 45:242-252 (2002).
Brodoff BN et al., "Biogenic-Amines and Diabetes in Sand Rat," Hormone and Metabolic Research 4:310 (1972).
Brunicardi FC et al., "Neural regulation of the endocrine pancreas," Int J Pancreatol 18:177-195 (1995).
Cegrell L "The occurrence of biogenic monoamines in the mammalian endocrine pancreas," Acta Physiol Scand Suppl 314:1-60 (1968).
Cegrell L et al., "Dopamine and 5-hydroxytryptamine in the guinea-pig pancreas," Life Sci 6:2483-2489 (1967).
Cetin Y "Biogenic amines in the guinea pig endocrine pancreas," Life Sci 50:1343-1350 (1992).
Davis FA et al., "Alkaloid synthesis using chiral δ-amino β-ketoesters: A stereoselective synthesis of (-)-Lasubine II," Org. Let., 2(17): 2623-2625 (2000).
Duttaroy A et al., "Muscarinic stimulation of pancreatic insulin and glucagon release is abolished in m3 muscarinic acetylcholine receptordeficient mice," Diabetes 53:1714-1720 (2004).
Eiden LE et al., "The vesicular amine transporter family (SLC18): amine/proton antiporters required for vesicular accumulation and regulated exocytotic secretion of monoamines and acetylcholine," Pflugers Arch 447:636-640 (2004).
El-Mansoury AM et al., "Activation of protein kinase C modulates alpha2-adrenergic signalling in rat pancreatic islets," Cell Signal 10:637-643 (1998).
Ekholm R et al., "Monoamines in the pancreatic islets of the mouse. Subcellular localization of 5-hydroxytryptamine by electron microscopic autoradiography" Diabetologia 7:339-348 (1971).
Erickson JD et al., "Distinct pharmacological properties and distribution in neurons and endocrine cells of two isoforms of the human vesicular monoamine transporter," Proc Natl Acad Sci USA 93:5166-5171 (1996).
Ericson et al., "Accumulation of Dopamine in Mouse Pancreatic B-Cells Following Injection of L-DOPA Localization to Secretory Granules and Inhibition of Insulin Secretion," Diabetologia, 13(2), pp. 117-124 (1977).
Feldman JM et al., "Characterization of pancreatic islet monoamine oxidase," Metabolism 24:581-588 (1975).
Feldman JM et al., "Monoamine oxidase inhibitors: nature of their interaction with rabbit pancreatic islets to alter insulin secretion," Diabetologia 11:487-494 (1975).

(56) References Cited

OTHER PUBLICATIONS

Gilon P et al., "Mechanisms and physiological significance of the cholinergic control of pancreatic beta-cell function," Endocr Rev 22:565-604 (2001).

Hansen SE et al., "Simultaneous determination of the content of serotonin, dopamine, noradrenaline and adrenaline in pancreatic islets isolated from fed and starved mice," Acta Endocrinol (Copenh) 86:820-832 (1977).

Hayashi M et al., "Secretory granule-mediated co-secretion of L-glutamate and glucagon triggers glutamatergic signal transmission in islets of Langerhans," J Biol Chem 278:1966-1974 (2003).

Henquin JC, "Triggering and amplifying pathways of regulation of insulin secretion by glucose," Diabetes 49:1751-1760 (2000).

Howell M et al., "Cloning and functional expression of a tetrabenazine sensitive vesicular monoamine transporter from bovine chromaffin granules," FEBS Lett 338:16-22 (1994).

Høy M et al., "Increase in cellular glutamate levels stimulates exocytosis in pancreatic beta-cells," FEBS Lett 531:199-203 (2002).

Iturriza FC et al., "Immunohistochemical investigation of tyrosine-hydroxylase in the islets of Langerhans of adult mice, rats and guinea pigs," Neuroendocrinology 57:476-480 (1993).

Jaim-Etcheverry G et al., "Electron microscopic cytochemistry of 5-hydroxytryptamine (5-HT) in the beta cells of guinea pig endocrine pancreas," Endocrinology 83:917-923 (1968).

Kenney C et al., "Tetrabenazine in the treatment of hyperkinetic movement disorders," Expert Rev Neurother 6:7-17 (2006).

Kitamura N et al., "An immunohistochemical survey of catecholamine-synthesizing enzyme-immunoreactive nerves and endocrine cells in the bovine pancreas," Anat Histol Embryol 28:81-84 (1999).

Koeppe et al., "11C-DTBZ and 18F-FDG PET Measures in Differentiating Dementias," J Nuclear Medicine 46:936-944 (2005).

Lake SP et al., "Large-scale purification of human islets utilizing discontinuous albumin gradient on IBM 2991 cell separator," Diabetes 38 Suppl 1:143-145 (1989).

Lakey JR et al., "Intraductal collagenase delivery into the human pancreas using syringe loading or controlled perfusion," Cell Transplant 8:285-292 (1999).

Lakey JR et al., "Variables in organ donors that affect the recovery of human islets of Langerhans," Transplantation 61:1047-1053 (1996).

Lane JD et al., "Neurochemical changes following the administration of depleters of biogenic monoamines," Life Sci 19:1663-1667 (1976).

Lenzen S et al., "Monoamine oxidase in pancreatic islets, exocrine pancreas, and liver from rats. Characterization with clorgyline, deprenyl, pargyline, tranylcypromine, and amezinium," Naunyn Schmiedebergs Arch Pharmacol 324:190-195 (1983).

Liu Y et al., "The role of vesicular transport proteins in synaptic transmission and neural degeneration," Annu Rev Neurosci 20:125-156 (1997).

Livak KJ et al., "Analysis of relative gene expression data using real-time quantitative PCR and the 2(-Delta Delta C(T)) Method," Methods 25:402-408 (2001).

Lübbers T et al., "1,3-Disubstituted 4-aminopiperidines as useful tools in the optimization of the 2-aminobenzo[a]quinolizine dipeptidyl peptidase IV inhibitors", Biorg Med Chem Lett., 2007, 17, 2966-2970.

* cited by examiner

Compound I

DTBZ

TBZ

GLUCOSE METABOLISM MODULATING COMPOUNDS

RELATED APPLICATIONS

This application is a U.S. National Stage Application of International Application No. PCT/US2009/02246, which was filed on Apr. 10, 2009, and which claims priority to U.S. Provisional Application Serial No. 61/123,785, which was filed on Apr. 11, 2008, all of which are incorporated by reference in their entireties as if recited in full herein.

GOVERNMENT FUNDING

This invention was made with government support under 5 R01 DK 63567, 1R21-DK70192-01, and 2 RO1 DK63567-05 awarded by the National Institutes of Health. The government has certain rights in the invention.

INCORPORATION BY REFERENCE OF SEQUENCE LISTING

This application contains references to amino acids and/or nucleic acid sequences that have been filed concurrently herewith as sequence listing text file "0314724ST25", file size of 1.39 KB, created on Sep. 28, 2010. The aforementioned sequence listing is hereby incorporated by reference in its entirety pursuant to 37 C.F.R. §1.52(e)(5).

FIELD OF THE INVENTION

The present invention relates, inter alia, to compounds, pharmaceutical compositions, and methods to modulate glucose metabolism and to prevent, treat, or ameliorate the effects of diabetes and hyperglycemia by, e.g., interacting with VMAT2.

BACKGROUND OF THE INVENTION

Diabetes mellitus is a growing epidemic affecting hundreds of millions of people worldwide. (Zimmer et al., 2001). Despite a recent explosion of new classes of hypoglycemic agents, the medical need remains largely unmet and innovative diagnostics and therapeutics are still urgently needed.

D-Glucose, with the synergistic effects of certain amino acids, is the major physiological stimulus for insulin secretion (reviewed in (Henquin 2000)). Net insulin production and glucose homeostasis, however, is regulated by a number of other molecules, including several classical neurotransmitters (Ahren 2000; Brunicardi, et al. 1995) that act directly on beta cells, and indirectly through other target tissues such as liver and skeletal muscle. Many of these molecules function as amplifying agents that have little or no effect by themselves, but enhance the signals generated by the beta cell glucose sensing apparatus (Henquin 2000). For example, during the cephalic phase of insulin release, acetylcholine (ACh) is released via islet parasympathetic innervation. Beta cells express the M3 muscarinic receptor (Duttaroy, et al. 2004) and respond to exogenous ACh with increased inositol phosphate production, which in turn facilitates sodium ($Na^+$) ion exit and calcium ion entry. This results in augmented insulin vesicle exocytosis (Barker, at al. 2002).

The amino acid glutamate, the major excitatory neurotransmitter in the central nervous system, is present in both alpha- and beta-cells of the endocrine pancreas. Glutamate is stored in glucagon-containing granules (Hayashi, et al. 2003), and is proposed to enhance insulin secretion when it is released into the vicinity of islet cells (Storto, et al. 2006). The presence of metabotropic glutamate receptors on alpha- and beta-cells themselves suggests the presence of both autocrine and paracrine circuits within islet tissue involved in the regulation of insulin secretion (Brice, et al. 2002).

Other neurotransmitters, such as the monoamines, epinephrine and norepinephine, acting both systemically and via nerve terminals in the vicinity of islets, may act to suppress glucose stimulated insulin secretion by direct interaction with adrenoreceptors expressed (mainly the alpha 2 receptor) on pancreatic beta cells (Ahren 2000; El-Mansoury and Morgan 1998). Beta cells of the endocrine pancreas also express dopamine receptors (D2) and respond to exogenous dopamine with inhibited glucose-stimulated insulin secretion (Ahren and Lundquist 1985; Niswender, et al. 2005; Rubi, et al. 2005; Shankar, et al. 2006). Purified islet tissue is a source of monoamines, and has been shown to contain 5-hydroxytryptamine, epinephrine, norepinephrine and dopamine (Cegrell 1968; Ekholm, et al. 1971; Hansen and Hedeskov 1977; Lundquist, et al. 1989; Niswender et al. 2005; Wilson, et al. 1974).

Beta cells also have the biosynthetic apparatus to create, dispose of, and store specific neurotransmitters. For example, tyrosine hydroxylase, the enzyme responsible for catalyzing the conversion of L-tyrosine to L-3,4-dihydroxyphenylalanine (L-DOPA), a precursor of dopamine, L-DOPA decarboxylase, responsible for converting L-DOPA to dopamine (Rubi et al. 2005) and dopamine beta hydroxylase, the enzyme that catalyzes the conversion of dopamine to norepinephrine, are present in islet tissue (Borelli, et al. 2003; Iturriza and Thibault 1993). Thus, L-DOPA is rapidly converted in islet beta-cells to dopamine (Ahren, et al., 1981; Borelli, et al. 1997).

Monoamine oxidase (MAO) is a catabolic enzyme responsible for the oxidative de-amination of monoamines, such as dopamine and catecholamines, and maintains the cellular homeostasis of monoamines. The possible role of MAO in islet function has been studied, (Adeghate and Donath 1991) and MAO has been detected in both alpha- and beta-cells of pancreatic islet cells, including beta cells (Feldman and Chapman 1975a, b). Interestingly, some MAO inhibitors have been shown to antagonize glucose-induced insulin secretion (Aleyassine and Gardiner 1975). The secretory granules of pancreatic beta cells store substantial amounts of calcium, dopamine and serotonin (Ahren and Lundquist 1985).

In the central nervous system, the storage of monoamine neurotransmitters in secretory organelles is mediated by a vesicular amine transporter. These molecules are expressed as integral membrane proteins of the lipid bilayer of secretory vesicles in neuronal and endocrine cells. An electrochemical gradient provides energy for the vesicular packaging of monoamines, such as dopamine, for later discharge into the synaptic space (reviewed by (Eiden, et al. 2004)). Both immunohistochemistry and gene expression studies show that islet tissue and the beta cells of the endocrine pancreas selectively express only one member of the family of vesicular amine transporters, vesicular monoamine transporter type 2 (VMAT2) (Anlauf, et al. 2003).

VMAT2 is one member of the vesicular transporter family responsible for the uptake and secretion of monoamine neurotransmitters in neurons and endocrine cells. (Zheng et al, 2006) Recent studies have shown the feasibility of noninvasive measurements of the amount of VMAT2 in the pancreas as a useful biomarker of beta cell mass both in humans (R. Goland, et al. 2009) and rodents (Souza, et al. 2006) using [$^{11}$C] dihydrotetrabenazine (DTBZ) and positron emission tomography, but the possible functional role of VMAT2, as expressed in islet tissue and beta cells, in glucose metabolism has not yet been explored.

As indicated, endogenously synthesized and/or stored monoamine neurotransmitters appear to participate in paracrine regulation of insulin secretion and entrainment of the activity of various cells within islets (Borelli and Gagliardino 2001). Given the important role of vesicular amine transporters in the storage and distribution of monoamine neurotransmitters, the possible of role of VMAT2 in glucose-stimulated insulin secretion was explored using the VMAT2-specific antagonist, tetrabenazine (TBZ) (Scherman, et al., 1983). TBZ acts as a reversible inhibitor of monoamine uptake into granular vesicles of presynaptic neurons (Pettibone, et al. 1984) through its ability to bind to VMAT2 (Scherman 1986) thereby facilitating monoamine degradation by MAO. Monoamine neurotransmitters that are depleted via VMAT2 inhibition by TBZ include serotonin, dopamine, and norepinephrine. Administration of TBZ to rats (plasma elimination with half life, $t_{1/2}$, equals 2 hours) reduces dopamine levels by 40%, serotonin by 44%, and norepinephrine by 41% in the brain (Lane, et al. 1976).

Although there are other vesicular amine transporters (e.g. vesicular monoamine transporter type 1, or VMAT1), tetrabenazine is highly specific for VMAT2, binds to the transporter with a dissociation constant in the nanomolar range, and displays a more than 10,000-fold reduced affinity towards VMAT1 (Erickson, et al. 1996; Varoqui and Erickson, 1997). Given the known effects of monoamine neurotransmitters on insulin secretion, the expression of VMAT2 by beta cells and the antagonist action of TBZ on monoamine transport, it would be desirable to identify compounds, pharmaceutical compositions and methods to modulate glucose metabolism and insulin secretion to, e.g., prevent, treat, or ameliorate the effects of impaired glucose metabolism, such as, e.g., diabetes and hyperglycemia.

SUMMARY OF THE INVENTION

Thus, one object of the invention is to show that VMAT2 expressed in beta cells of the endocrine pancreas plays a role in the regulation of insulin production and glucose homeostasis in vivo. Another object of the invention is to show that the glucose tolerance enhancing effects of TBZ is mediated by the depletion of dopamine following the antagonism of VMAT2. A further object of the invention is to show that certain compounds modulate blood glucose levels. These and other objects of the invention are disclosed in more detail in the embodiments that follow.

One embodiment of the present invention is a compound of formula I:

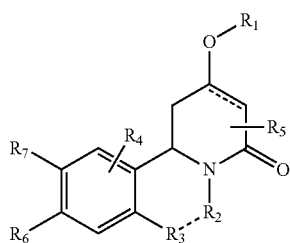

wherein $R_1$, $R_2$, $R_3$, $R_6$, and $R_7$ are independently selected from H, halogen, hydroxyl, $C_{1-8}$alkyl, $C_{1-8}$alkenyl, $C_{1-8}$alkynyl, $C_{1-8}$alkoxy, 3- to 8-membered carbocyclic or heterocyclic, aryl, heteroaryl, $C_{1-4}$aralkyl, residues of glycolic acid, ethylene glycol/propylene glycol copolymers, carboxylate, ester, amide, carbohydrate, amino acid, alditol, $OC(X)_2COOH$, $SC(X)_2COOH$, NHCHXCOOH, COY, $CO_2Y$, sulfate, sulfonamide, sulfoxide, sulfonate, sulfone, thioalkyl, thioester, propylphthalimide, and thioether;

$R_4$ and $R_5$, which are attached to one or more positions of at least one carbon atom of the respective rings, are independently selected from H, halogen, hydroxyl, $C_{1-8}$alkyl, $C_{1-8}$alkenyl, $C_{1-8}$alkynyl, $C_{1-8}$alkoxy, 3- to 8-membered carbocyclic or heterocyclic, aryl, heteroaryl, $C_{1-4}$aralkyl, residues of glycolic acid, ethylene glycol/propylene glycol copolymers, carboxylate, ester, amide, carbohydrate, amino acid, alditol, $OC(X)_2COOH$, $SC(X)_2COOH$, NHCHXCOOH, COY, $CO_2Y$, sulfate, sulfonamide, sulfoxide, sulfonate, sulfone, thioalkyl, thioester, propylphthalimide, and thioether;

X is selected from H, $C_{1-8}$alkyl, $C_{1-8}$alkenyl, $C_{1-8}$alkynyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

Y is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and ----- is an optional bond, wherein the optional bond is a single bond or a double bond;

or an enantiomer, optical isomer, diastereomer, N-oxide, crystalline form, hydrate, or pharmaceutically acceptable salt thereof.

Another embodiment of the present invention is a compound having the structure (1):

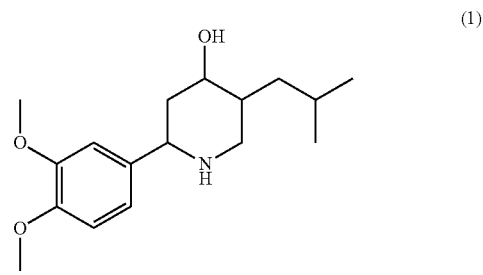 [SMILES: COc1ccc(C2CC(O)C(CC(C)C)CN2)cc1OC]

or an enantiomer, optical isomer, diastereomer, N-oxide, crystalline form, hydrate, or pharmaceutically acceptable salt thereof.

A further embodiment of the present invention is a pharmaceutical composition comprising a pharmaceutically acceptable carrier and a therapeutically effective amount of a compound according to the present invention.

Yet another embodiment of the present invention is a method for modulating blood glucose levels in a subject comprising administering to a subject an effective amount of a compound according to the present invention.

An additional embodiment of the present invention is a method for preventing, treating, or ameliorating the effects of diabetes in a subject comprising administering to a subject an effective amount of a compound according to the present invention.

A further embodiment of the present invention is a method for preventing, treating, or ameliorating the effects of hyperglycemia comprising administering to a subject an effective amount of a compound according to the present invention.

Yet another embodiment of the present invention is a method for modulating blood glucose levels in a subject comprising administering to a subject an effective amount of a pharmaceutical composition according to the present invention.

Another embodiment of the present invention is a method for preventing, treating, or ameliorating the effects of diabetes in a subject comprising administering to a subject an effective amount of a pharmaceutical composition according to the present invention.

A further embodiment of the present invention is a method for preventing, treating, ameliorating the effects of hyperglycemia comprising administering to a subject an effective amount of a pharmaceutical composition according to the present invention.

BRIEF DESCRIPTION OF THE DRAWINGS

FIG. 1A shows the blood glucose values during IPGTT of Lewis rats treated with vehicle alone (open symbol) or with tetrabenazine at the indicated doses. Error bars indicate the standard error of the mean (S.E.M.) (n=25) at the indicated dose (closed symbols). FIG. 1B shows the results presented as AUC (area under the curve) IPGTT. The asterisk indicates AUC IPGTT for vehicle controls (n=25) was significantly higher than the AUC IPGTT of the same TBZ treated animals (n=25) ($p<0.05$). The double asterisk indicates that the AUC IPGTT following treatment with TBZ and L-DOPA was significantly different than that of TBZ alone (n=6). Error bars represent S.E.M.

FIG. 5A shows the products of the qRT-PCR assay on total RNA from: brain, purified islets and total pancreas using VMAT2 primers that specifically amplify a 175 base pair (bp) fragment. Untranscribed RNA from purified islets was used as a control. GelPilot 200 bp ladder was the molecular weight standard. FIG. 5B shows the relative accumulation of VMAT2 mRNA in pancreata of control and streptozotocin-induced diabetic Lewis rats. The average accumulation of VMAT2 mRNA in streptozotocin-treated rodents was approximately eight-fold lower than the average accumulation in untreated pancreata ($p<0.005$) FIG. 5C shows a Western blot analysis of VMAT2 expression in protein lysates prepared from control and streptozotocin-induced diabetic Lewis rats.

FIG. 7A shows the blood glucose concentration versus time curves for three repeat experiments with vehicle, TBZ, and compound 8 performed in a single rodent. FIG. 7B shows AUC IPGTT for a number of compounds according to the present invention. The area under the curve (AUC) IPGTT was calculated by the trapezoidal rule. Error bars indicate S.E.M. (n=5). The statistical significance of the difference between drug and vehicle was calculated by the method of Student. A p value of less than 0.005 is shown by an asterisk. The p value of the difference between the average AUC IPGTT of TBZ and compound 8 was 0.030.

DETAILED DESCRIPTION OF THE INVENTION

Figure 1:
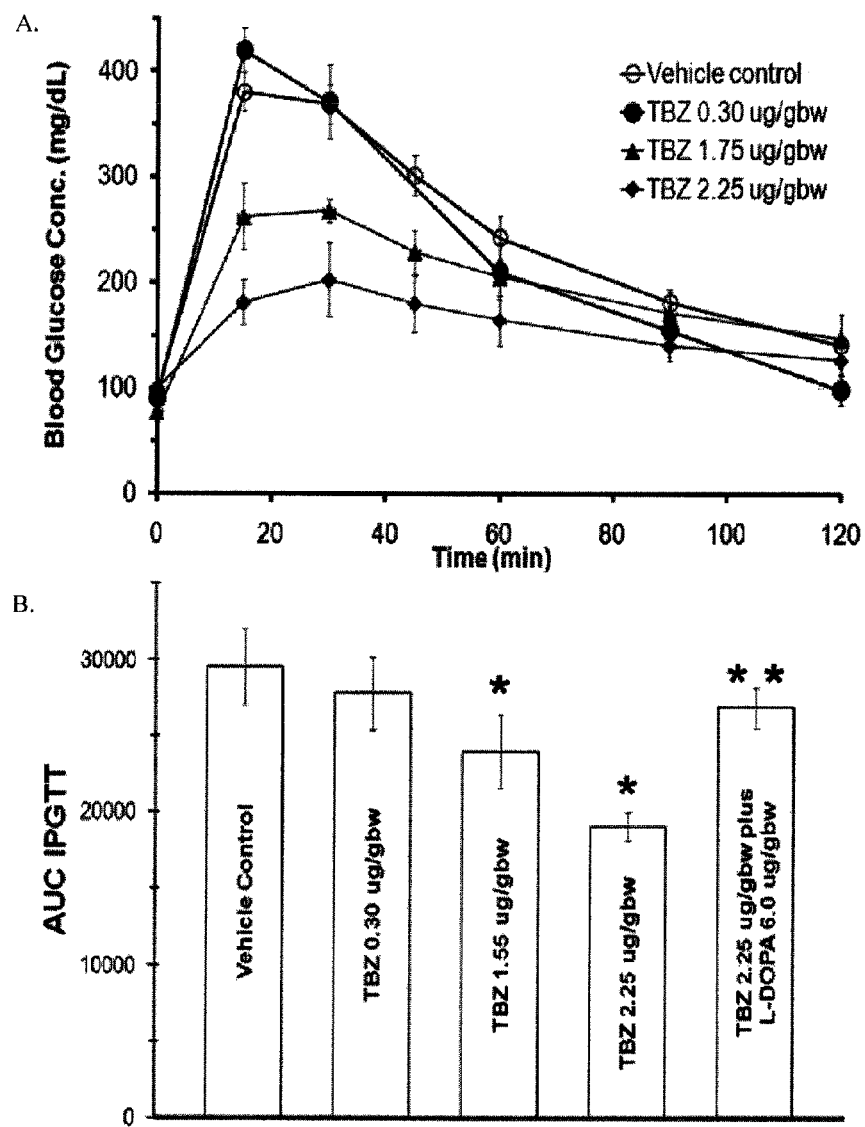
FIG. 1 demonstrates that tetrabenazine reduces the blood glucose excursion during an intraperitoneal glucose tolerance test (IPGTT).

One embodiment of the present invention is a compound of formula I:

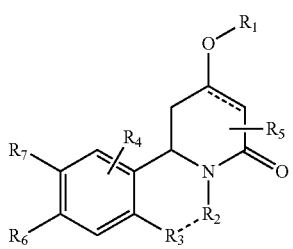

I wherein $R_1$, $R_2$, $R_3$, $R_6$, and $R_7$ are independently selected from H, halogen, hydroxyl, $C_{1-8}$alkyl, $C_{1-8}$alkenyl, $C_{1-8}$alkynyl, $C_{1-8}$alkoxy, 3- to 8-membered carbocyclic or heterocyclic, aryl, heteroaryl, $C_{1-4}$aralkyl, residues of glycolic acid, ethylene glycol/propylene glycol copolymers, carboxylate, ester, amide, carbohydrate, amino acid, alditol, $OC(X)_2COOH$, $SC(X)_2COOH$, NHCHXCOOH, COY, $CO_2Y$, sulfate, sulfonamide, sulfoxide, sulfonate, sulfone, thioalkyl, thioester, propylphthalimide, and thioether;

$R_4$ and $R_5$, which are attached to one or more positions of at least one carbon atom of the respective rings, are independently selected from H, halogen, hydroxyl, $C_{1-8}$alkyl, $C_{1-8}$alkenyl, $C_{1-8}$alkynyl, $C_{1-8}$alkoxy, 3- to 8-membered carbocyclic or heterocyclic, aryl, heteroaryl, $C_{1-4}$aralkyl, residues of glycolic acid, ethylene glycol/propylene glycol copolymers, carboxylate, ester, amide, carbohydrate, amino acid, alditol, $OC(X)_2COOH$, $SC(X)_2COOH$, NHCHXCOOH, COY, $CO_2Y$, sulfate, sulfonamide, sulfoxide, sulfonate, sulfone, thioalkyl, thioester, propylphthalimide, and thioether;

X is selected from H, $C_{1-8}$alkyl, $C_{1-8}$alkenyl, $C_{1-8}$alkynyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

Y is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and ----- is an optional bond, wherein the optional bond is a single bond or a double bond;

or an enantiomer, optical isomer, diastereomer, N-oxide, crystalline form, hydrate, or pharmaceutically acceptable salt thereof. In the present invention, it is to be understood that each R group (e.g., $R_1$-$R_9$) includes all possible combinations of the specific members recited in each R group.

In one aspect of this embodiment, the compound has formula II:

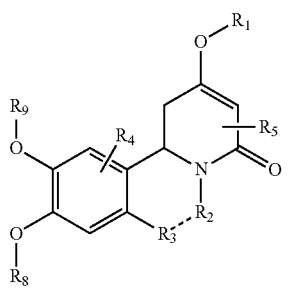

II wherein $R_1$, $R_2$, $R_3$, $R_8$ and $R_9$ are independently selected from the group consisting of H, halogen, $C_1$-$C_8$ alkyl, $C_1$-$C_8$alkenyl, and $C_1$-$C_8$alkynyl;

$R_4$ and $R_5$, which are attached to one or more positions of at least one carbon atom of the respective rings, are independently selected from H, halogen, hydroxyl, $C_{1-8}$alkyl, $C_{1-8}$alkenyl, $C_{1-8}$alkynyl, $C_{1-8}$alkoxy; and ----- is an optional bond, wherein the optional bond is a single bond or a double bond;

or an enantiomer, optical isomer, diastereomer, N-oxide, crystalline form, hydrate, or pharmaceutically acceptable salt thereof.

Preferably, the compound has formula III:

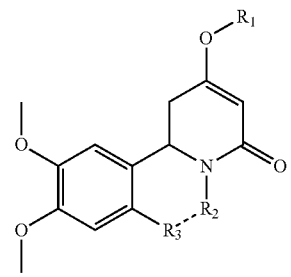

III wherein $R_1$, $R_2$, and $R_3$ are independently selected from the group consisting of H, $C_1$-$C_8$alkyl, $C_1$-$C_8$alkenyl, and $C_1$-$C_8$alkynyl; and ----- is an optional bond, wherein the optional bond is a single bond or a double bond;

or an enantiomer, optical isomer, diastereomer, N-oxide, crystalline form, hydrate, or pharmaceutically acceptable salt thereof.

More preferably, the compound has formula III, wherein $R_1$ is selected from the group consisting of H, $C_1$-$C_8$alkyl, $C_1$-$C_8$alkenyl, and $C_1$-$C_8$alkynyl; $R_2$ and $R_3$ are selected from the group consisting of H and $C_1$alkyl; and ----- is a single bond if $R_2$ or $R_3$ is not H.

In another preferred embodiment, the compound is compound 15:

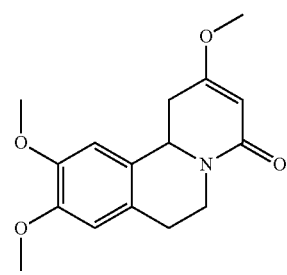

(15)

or an enantiomer, optical isomer, diastereomer, N-oxide, crystalline form, hydrate, or pharmaceutically acceptable salt thereof.

In another aspect of this embodiment, the compound has formula IV:

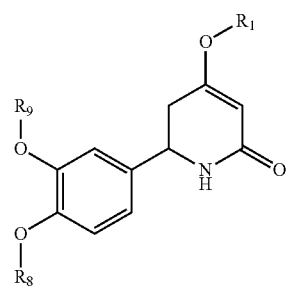

IV wherein $R_1$, $R_8$, and $R_9$ are independently selected from the group consisting of H, halogen, hydroxyl, $C_{1-8}$alkyl, $C_{1-8}$alkenyl, $C_{1-8}$alkynyl, $C_{1-8}$alkoxy, 3- to 8-membered carbocyclic or heterocyclic, aryl, heteroaryl, $C_{1-4}$aralkyl, residues of glycolic acid, ethylene glycol/propylene glycol copolymers, carboxylate, ester, amide, carbohydrate, amino acid, alditol, $OC(X)_2COOH$, $SC(X)_2COOH$, NHCHXCOOH, COY, $CO_2Y$, sulfate, sulfonamide, sulfoxide, sulfonate, sulfone, thioalkyl, thioester, propylphthalimide, and thioether;

X is selected from H, $C_{1-8}$alkyl, $C_{1-8}$alkenyl, $C_{1-8}$alkynyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent;

Y is selected from H, $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent;

or an enantiomer, optical isomer, diastereomer, N-oxide, crystalline form, hydrate, or pharmaceutically acceptable salt thereof.

Non-limiting examples of a compound according to the present invention include:

(1) a compound having formula IV, wherein $R_1$ is —$CH_2$—CH—$(CH_3)_2$ and $R_8$, and $R_9$ are as set forth in the previous paragraph;

(2) a compound having formula IV, wherein $R_8$ is methyl, and $R_1$ and $R_9$ are as set forth in the previous paragraph;

(3) a compound having formula IV, wherein $R_9$ is methyl, and wherein $R_1$ and $R_8$ are as set forth in the previous paragraph;

(4) a compound having formula IV, wherein both $R_8$ and $R_9$ are methyl, and $R_1$ is as set forth in the previous paragraph;

(5) a compound having formula IV, wherein $R_1$ is selected from $C_{1-8}$alkyl, $C_{1-8}$alkenyl, $C_{1-8}$alkoxy, and $R_8$ and $R_9$ are both methyl;

(6) compound 8:

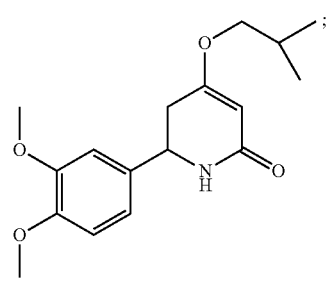

(8)

or (7) an enantiomer, optical isomer, diastereomer, N-oxide, crystalline form, hydrate, or pharmaceutically acceptable salt of any of the compounds listed in (1)-(6).

Another embodiment of the present invention is a compound having the structure (1):

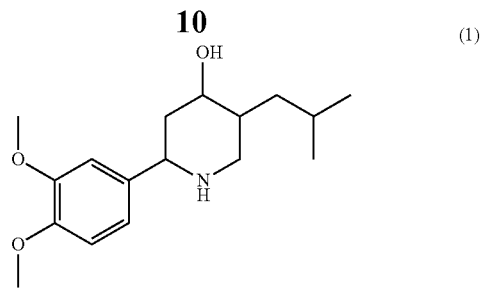

(1)

or an enantiomer, optical isomer, diastereomer, N-oxide, crystalline form, hydrate, or pharmaceutically acceptable salt thereof.

A further embodiment of the present invention is a pharmaceutical composition comprising a pharmaceutically acceptable carrier and a therapeutically effective amount of a compound according to the present invention, including those compounds set forth above. Preferably, the pharmaceutical composition includes a therapeutically acceptable amount of a compound according to formula I, compound 8, compound 15, or combinations thereof.

Yet another embodiment of the present invention is a method for modulating blood glucose levels in a subject. This method comprises administering to a subject an effective amount of a compound or a pharmaceutical composition according to the present invention. Preferably, the compound is a compound of formula I, compound 8, compound 15, or combinations thereof. Preferably, the pharmaceutical composition includes a therapeutically acceptable amount of a compound according to formula I, compound 8, compound 15, or combinations thereof. In one aspect of this embodiment, the compound or pharmaceutical composition acts by interacting with, e.g., binding to, VMAT2 to provide the modulation.

As used herein in relation to blood glucose levels, "modulate," "modulating," and like terms mean to increase or, preferably, to decrease the blood glucose levels in a mammal, e.g., a human patient, administered a compound or pharmaceutical composition according to the present invention relative to a patient who is not administered the compound.

An additional embodiment of the present invention is a method for preventing, treating, or ameliorating the effects of diabetes (such as type I or type II diabetes) in a subject. This method comprises administering to a subject an effective amount of a compound or a pharmaceutical composition according to the present invention. Preferably, the compound is a compound of formula I, compound 8, compound 15, or combinations thereof. Preferably, the pharmaceutical composition includes a therapeutically acceptable amount of a compound according to formula I, compound 8, compound 15, or combinations thereof. In one aspect of this embodiment, the compound or pharmaceutical composition acts by interacting with, e.g., binding to, VMAT2 to prevent, treat, or ameliorate the effects of diabetes.

A further embodiment of the present invention is a method for preventing, treating, or ameliorating the effects of hyperglycemia. This method comprises administering to a subject an effective amount of a compound or a pharmaceutical composition according to the present invention. Preferably, the compound is a compound of formula I, compound 8, compound 15, or combinations thereof. Preferably, the pharmaceutical composition includes a therapeutically acceptable amount of a compound according to formula I, compound 8, compound 15, or combinations thereof. In one aspect of this embodiment, the compound or pharmaceutical composition acts by interacting with, e.g., binding to, VMAT2 to prevent, treat, or ameliorate the effects of hyperglycemia.

In the present invention, an "effective" amount or "therapeutically effective" amount of a compound or a pharmaceutical composition is an amount of such a compound or a pharmaceutical composition that is sufficient to effect beneficial or desired results as described herein when administered to a subject such as a mammal, preferably a human, in need of such therapy, e.g., who is suffering from diabetes or hyperglycemia. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a compound or a pharmaceutical composition according to the invention will be that amount of the compound or the pharmaceutical composition, which is the lowest dose effective to produce the desired effect with no or minimal side effects.

Suitable, non-limiting examples of dosages of a compound or pharmaceutical composition according to the present invention is from about 1 ng/kg to about 1000 mg/kg, such as from about 0.1-1.0 µg/gm, including 0.20-0.80 µg/gm, as well as e.g., about 1 mg/kg to about 100 mg/kg, including from about 5 mg/kg to about 50 mg/kg. Other representative dosages of a compound or a pharmaceutical composition according to the present invention include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg or those dosages disclosed in the present Examples. The effective dose of a compound/pharmaceutical composition may be administered as two, three, four, five, six or more sub-doses, administered separately at appropriate intervals throughout the day.

A pharmaceutical composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a pharmaceutical composition of the present invention may be administered in conjunction with other treatments. A pharmaceutical composition of the present invention may be encapsulated or otherwise protected against gastric or other secretions, if desired.

The pharmaceutically acceptable compositions of the invention comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, Pa.).

Pharmaceutically acceptable carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the invention may, optionally, contain additional ingredients and/or materials commonly used in such pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

In the present invention, the following definitions apply.

As used herein, the term "acyl" has its art-recognized meaning and refers to a group represented by the general formula hydrocarbylC(O)—, preferably alkylC(O)—.

As used herein, the term "acylamino" has its art-recognized meaning and refers to an amino group substituted with an acyl group and may be represented, for example, by the formula hydrocarbylC(O)NH—.

As used herein, the term "alditol" means any of a class of acyclic alcohols containing multiple hydroxyl groups, which are derived from a monosaccharide containing a terminal carbonyl group and having a chemical formula of the form $C_n(H_2O)_n$ by reduction of the carbonyl functional group. Alditol includes, for example, sorbitol.

The term "alkoxy" refers to an alkyl group, preferably a lower alkyl group, having an oxygen attached thereto. Representative alkoxy groups include methoxy, ethoxy, propoxy, isopropoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 8 or fewer carbon atoms in its backbone (e.g., $C_1$-$C_8$ for straight chains, $C_3$-$C_8$ for branched chains). Likewise, preferred cycloalkyls have from 3-8 carbon atoms in their ring structure, including 5, 6 or 7 carbons in the ring structure.

Moreover, unless otherwise indicated, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aromatic, or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, alkyl, alkenyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylaryl", as used herein, refers to an aryl group substituted with an alkyl group.

The term "alkylheteroaryl", as used herein, refers to a heteroaryl group substituted with an alkyl group.

The term "alkylheterocycle", as used herein, refers to an heterocycle group substituted with an alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

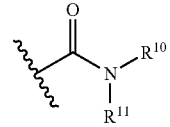

wherein $R^{10}$ and $R^{11}$ each independently represent a hydrogen or hydrocarbyl group, or $R^{10}$ and $R^{11}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

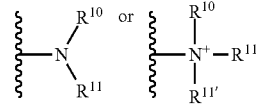

wherein $R^{10}$, $R^{11}$, and $R^{11'}$ each independently represent a hydrogen or a hydrocarbyl group, or $R^{10}$ and $R^{11}$ taken together with the N atom to which they are attached complete a heterocycle having from 4 to 8 atoms in the ring structure.

The term "amino acid," as used herein, refers a functional group containing both amine and carboxyl groups.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

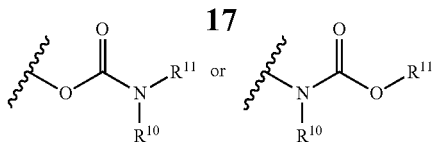

wherein $R^{10}$ and $R^{11}$ independently represent hydrogen or a hydrocarbyl group.

The terms "carbocycle", "carbocyclyl", and "carbocyclic", as used herein, refer to a non-aromatic saturated or unsaturated ring in which each atom of the ring is carbon. Preferably a carbocycle ring contains from 3 to 8 atoms, including 5 to 7 atoms, such as for example, 6 atoms.

The term "carbohydrate", as used herein, is a functional group that includes an aldehyde or ketone group with many hydroxyl groups added to the carbon backbone, usually one on each carbon atom that is not part of the aldehyde or ketone functional group. Carbohydrate include monosaccharides such as glucose, galactose, and fructose. Carbohydrate also include oligosaccharides made of two or more monosaccharides, but preferably two monosaccharides.

The terms "carboxy" and "carboxyl", as used herein, refer to a group represented by the formula —$CO_2H$.

The term "carboxylate" refers to the conjugate base of a carboxyl group, represented by the formula —$COO^-$.

The term "ester", as used herein, refers to a group —C(O)O$R^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" are used interchangeably herein and mean halogen and include chloro, fluoro, bromo, and iodo.

The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heteroaromatic" means at least one carbon atoms in the aromatic group is substituted with a heteroatom.

The terms "heterocyclyl", "heterocycle", "heterocyclic", and the like refer to substituted or unsubstituted non-aromatic ring structures, preferably 3- to 8-membered rings, whose ring structures include at least one heteroatom, preferably one to four heteroatoms, more preferably one or two heteroatoms. The terms "heterocyclyl," "heterocyclic," and the like also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, alkyl, alkenyl, alkynyl, or alkoxy is meant to include groups where there are ten or fewer non-hydrogen atoms in the substituent, preferably eight or fewer, such as for example, from about 2 to 8 carbon atoms, including less than 6 carbon atoms. A "lower alkyl", for example, refers to an alkyl group that contains ten or fewer carbon atoms, preferably eight or fewer. In certain embodiments, acyl, alkyl, alkenyl, alkynyl, or alkoxy substituents defined herein are respectively lower acyl, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 3 to 8, such as for example, 5 to 7.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As used herein, the term "substituent," means H, cyano, oxo, nitro, acyl, acylamino, halogen, hydroxy, amino acid, amine, amide, carbamate, ester, ether, carboxylic acid, thio, thioalkyl, thioester, thioether, $C_{1-8}$ alkyl, $C_{1-8}$ alkoxy, $C_{1-8}$ alkenyl, $C_{1-8}$ aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, and arylsulfonyl.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

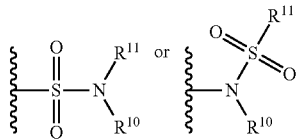

wherein $R^{10}$ and $R^{11}$ independently represents hydrogen or hydrocarbyl.

The term "sulfoxide" is art-recognized and refers to the group —$S(O)$—$R^7$, wherein $R^7$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^7$, wherein $R^7$ represents a hydrocarbyl.

The term "thioalkyl", as used herein, refers to an alkyl group substituted with a thiol group.

The term "thioester", as used herein, refers to a group —$C(O)SR^7$ or —$SC(O)R^7$ wherein $R^7$ represents a hydrocarbyl.

The term "thioether", as used herein, is equivalent to an ether, wherein the oxygen is replaced with a sulfur.

The following examples are provided to further illustrate the methods of the present invention. These examples are illustrative only and are not intended to limit the scope of the invention in any way.

EXAMPLES

Example 1

Materials and Methods
Drugs and Reagents

L-epinephrine bitartrate, D-glucose, L-DOPA, sodium citrate were obtained from Sigma Chemicals.

All cell culture media and supplements were obtained from Invitrogen (Carlsbad, Calif.). Tissue culture plates were obtained from Falconware (Becton-Dickinson, Inc., Oxnard, Calif.). Tetrabenazine and dihydrotetrabenazine were obtained from the National Institute of Mental Health's Chemical Synthesis and Drug Supply Program or Tocris Bioscience (Ellisville, Mo.). All other chemicals (other than the compounds synthesized as described below) were of the highest commercial quality available.

Experimental Animals

All animal studies were reviewed and approved by the Institutional Animal Care and Use Committee (IACUC) at Columbia University's College of Physicians and Surgeons. All experiments were performed in accordance with 'Principles of laboratory animal care' (NIH publication no. 85-23, revised 1985). Normal male Lewis rats were obtained from Taconic (Taconic Inc., Germantown, N.Y.) and were housed under conditions of controlled humidity (55±5%), temperature (23±1° C.), and lighting (light on from 6 a.m. to 6 p.m.) with free access to standard laboratory Purina rat chow and water.

Rats were handled daily to minimize nonspecific stress for more than 7 days before the experiments began. In most experiments, it was necessary to measure blood glucose in fasting animals. For these groups, food was removed at the beginning of the light cycle, 6 hours before glucose levels were tested. Fasting rats for longer than eight hours resulted in higher experimental variability.

Sixty minutes prior to intraperitoneal glucose tolerance testing (IPGTT), anesthesia of male Lewis rats was induced with isoflurane (3-4% in oxygen) and maintained with 1-2% isoflurane in oxygen.

Anaesthetized rats were administered TBZ at the indicated dose by intravenous (i.v.) injection using the penile vein. TBZ or L-DOPA was dissolved in neat sterile DMSO and diluted (always more than 10 fold) in sterile saline. Control rats received injections of vehicle alone (10% DMSO in Saline).

Animals were fully recovered for at least 30 minutes before receiving IPGTT. In specified experiments, L-DOPA was injected interperitoneal (I.P.) at the specified dose at the initiation of IPGTT. Abnormal glucose tolerance was induced by a single I.P. injection of streptozotocin (STZ) (Sigma Aldrich, St. Louis, Mo.) (50 mg/kg) to animals that had been fasted 4 hours to enhance the efficacy of STZ.

STZ solution was prepared fresh by dissolving it in 0.1 M citrate buffer (pH 5.5) and terminally sterile filtered. Control Lewis age and weight matched rats received a 0.5 ml/kg citrate vehicle alone via intraperitoneal injection. The diabetic phenotype induced by STZ was allowed to develop for one week before confirmation by glucose tolerance testing. Animals were considered to have a stable diabetic phenotype after three consecutive measurements of blood glucose with a value of greater than 300 mg/dl. Animals failing this criterion were not used and euthanized.

Blood Glucose, Insulin, Glucagon and Intraperitoneal Glucose Tolerance Tests Measurements Blood samples were collected between 12:00 noon and 2:00 p.m. from a superficial blood vessel in the tails of the rats following 6 hours of fasting. The fasting blood glucose (BG) levels of the rats were measured using an Accu-Check blood glucose monitoring system (Roche Diagnostics, Sommerville, N.J.). IPGTT was performed in 6-hour fasting anaesthetized animals as previously described (Weksler-Zangen, et al. 2001). Briefly, after baseline BG measurements, animals received an I.P. injection of 2 grams of glucose/kg body weight. To minimize stress during the procedure, rats were handled by the same operator during acclimatization and later during weighing and IPGTT. Blood samples (50 μl or 150 μl) were collected at baseline and then again 15, 30, 60, 90, and 120 minutes following I.P. injection of glucose. Blood glucose concentrations were measured immediately on these samples and the remainder processed. Plasma was immediately separated by centrifugation at 3,000×g for 15 minutes and then stored at −80° C. until analysis.

Insulin and glucagon concentration measurements in rat plasma were performed by ELISA as per the manufacturer's instructions using kits from Linco Research Inc. (St. Charles, Mich.) and Alpco Diagnostics (Salem, N.H.), respectively. To validate the test, saline injections were performed by the same method. During this experiment, glucose concentration did not differ from baseline at each time point (data not shown). The area under the insulin, glucagon and IPGTT glucose concentration×time curve (AUC IPGTT) was calculated by the trapezoidal rule.

Islet Tissue and Glucose Stimulated Insulin Secretion

Rat pancreas digestion, islet isolations, and static insulin secretion assays were performed as previously described (Niswender et al. 2005; Sweet, et al. 2004; Sweet and Gilbert 2006). Purified islets were cultured in RPMI 1640 culture media with 10% fetal bovine serum at 37° C. in humidified air (5% $CO_2$) for 18 to 24 hours. Assessment of insulin secretion in static media was carried out as follows. Islets were hand-picked twice into a Petri dishes containing Krebs-Ringer bicarbonate (KRB) buffer (with 3 mM glucose and 0.1% BSA) and pre-incubated for 60 minutes (37° C. and 5% $CO_2$). Subsequently, batches of 100 islets (in quadruplicate) were transferred into 96-well plates containing 200 μl of KRB with either 3 or 20 mM glucose, with or without 100 nM DTBZ and incubated for 60 minutes. The supernatant was removed and the insulin was measured using ELISA (ALPCO, Windham, N.H.).

The Effect of DTBZ on Dipeptidyl Peptidase IV (DPP-IV)

The effect of DTBZ on DDP-IV was determined using the DPP profiling service from BPS Bioscience, Inc. (San Diego, Calif.).

Dopamine Measurements

Anaesthetized rats received an intravenous injection of TBZ and were sacrificed one hour later.

Euthanasia was performed by exsanguination of the anesthetized animal. Brain and pancreas were harvested as quickly as possible and frozen at −80° C. until use. Frozen tissue was pulverized in a liquid nitrogen-cooled mortar and extracted in 0.01 N hydrochloric acid (HCl). The tissue extract was centrifuged at 10,000×g at 4° C. to remove debris and the total protein was estimated by reading the absorbance at 280 nm. The concentration of dopamine in the extract was estimated using an ELISA kit from Rocky Mountain Diagnostics (Colorado Springs, Colo.) as per the manufacturer's instructions and normalized to the extract protein concentration.

Quantitation of VMAT2 mRNA in Pancreata and Islets of Lewis Rats.

Harvesting of pancreata was performed as follows. Anesthsized rats were opened with a midline incision and the liver, stomach, and small intestines reflected to expose the pancreas. The cavity was then bathed with 10 ml of a 1:1 solution PBS1× and RNAlater (Ambion, Austin, Tex.). The pancreas was dissected and transferred to a 50 ml polypropylene tube containing 6 ml of fresh RNAlater solution and—if not immediately processed—stored at −80° C. After thawing, the entire pancreas was transferred into 1 ml of QIAzol (QIAGEN, Valencia, Calif.)/100 mg of tissue and homogenized. In the indicated experiments, purified and hand picked rat islets (about 500) were transferred directly to QIAzol. Total RNA, either from pancreata or purified islets, was purified using the RNeasy Mini Kit (QIAGEN, Valencia, Calif.) in conjunction with the RNase-Free DNase Set (QIAGEN, Valencia, Calif.). All RNA extractions were performed using RNase-/DNase-free laboratory ware. RNA was quantified and assessed for purity by electrophoresis on a 1.6% agarose gel and UV spectrophotometry. Tissue processing, RNA extraction, and qRT-PCR assay set up were performed in separate designated laboratory areas to prevent cross-contamination. All reverse transcriptase reactions were performed using the SuperScript III RT System from INVITROGEN (Carlsbad, Calif.) with random-priming. The qPCR assays were performed using the amount of cDNA obtained by retro-transcribing 100 ng of total RNA.

The QuantiTect SYBR Green PCR Kit (INVITROGEN (Carlsbad, Calif.)) was used to perform all the reactions in the presence of 0.2 μM primers, in a total volume of 25 μl. Samples were amplified with a precycling hold at 95° C. for 15 minutes, followed by 36 cycles of denaturation at 95° C. for 15 seconds, annealing at 55° C.-60° C. (depending from the primers) for 30 seconds, and extension at 72° C. for 20 seconds. qRT-PCR reagent controls (reagents without any template or with 100 ng of not retro-transcribed RNA) were included in all the assays. Each assay was run in triplicate and repeated at least twice to verify the results, and the mean copy number was used for analysis. The standard deviation between assays was not significant (5%) in all the experiments. The relative amount of specific transcripts was calculated as previously described (Maffei, et al. 2004). To correct for sample to sample variations in qRT-PCR efficiency and errors in sample quantitation, the level of both GAPDH transcripts and 18S rRNA was tested for use in normalization of specific RNA levels. In these experiments no significant differences were found between normalization by GAPDH mRNA level or normalization by 18S rRNA levels. All oligonucleotides were synthesized by INVITROGEN (Carlsbad, Calif.). The primer sequences were as follows: 5'-CGC AAA CTG ATC CTG TTC AT-3' (VT2-2 F) (SEQ ID NO: 1) and 5'-AGA AGA TGC TTT CGG AGG TG-3' (VT2-2 R) (SEQ ID NO: 2); 5'-AAC GGA TTT GGC CGT ATC GGA C-3' (rGAPDH F) (SEQ ID NO: 3) and 5'-TCG CTC CTG GAA GAT GGT GAT G-3' (rGAPDH R) (SEQ ID NO: 4); 5'-TTS GAA CGT CTG CCC TAT CAA-3' (r18S F) (SEQ ID NO: 5) and 5'-CAA TTA CAG GGC CTC GAA AG-3' (r18S R) (SEQ ID NO: 6). The relative amounts of mRNA, were calculated by the comparative cycle threshold (CT) method described by Livak and Schmittgen (Livak and Schmittgen 2001).

Quantitation of VMAT2 and Preproinsulin Protein in Pancreas Lysates by Western Blot.

Western blot analysis was conducted on pancreas tissue obtained from control and diabetic STZ treated rats using standard procedures. Briefly, sample tissues were flash frozen in liquid nitrogen and ground to a fine powder while frozen. Powdered proteins were solubilized in 1× PBS; 1% Nonidet P-40; 0.5% sodium deoxycholate and 0.1% SDS. A complete cocktail of mammalian protease inhibitors (Sigma-Aldrich, St. Louis, Mo.), at high concentration, was added immediately prior to sample preparation. Protein concentrations were determined using a Bio-Rad protein assay (Bio-Rad Inc., Hercules, Calif.) with bovine serum albumin standards and following the manufacturers recommendations. Solubilized proteins were diluted in Laemmli sample buffer and incubated at 100° C. for 1 minute. Protein separation was conducted using the Bio-Rad Lab Mini-gel electrophoresis system on 15% Acrylamide/Bis gels. Proteins were then transferred onto Immobilon-PVDF membranes using the same system. Membranes were prepared for immunoblotting by washing in TTBS (10 mM Tris-Glycine, pH 8.0, 0.15 M NaCl, with 0.05% (w/v) Tween-20). Membranes were then blocked in TTBS plus 5% (w/v) non-fat dry milk. The membranes were separated into high (>15 kD) and low MW (<15 kd) ranges. Membranes were probed for specific proteins by overnight incubation with either a 1:1,000 dilution of rabbit anti-VMAT2 primary antibody (Chemicon International, Temecula, Calif.) or a 1:400 dilution anti-insulin primary antibody (Abcam, Cambridge, Mass.). The membranes were then washed three times in TTBS and developed with 1:5,000 dilution of either donkey anti-rabbit antibodies or sheep anti-mouse antibodies conjugated to horseradish peroxidase (Amersham Bioscience, Pittsburgh, Pa.). After one hour, the membranes were washed in TTBS, and a chemiluminescent substrate solution was added (Immobilon Western Solution (Millpore, Bedford, Mass.)). Membranes were then used to expose Bio-Max film (Eastman Kodak, Rochester, N.Y.).

Statistical Analysis

All results are presented as means±S.E.M., or as indicated in the text. Students T testing was performed for assessing statistical significance of differences. All p values are 2-tailed.

PET Study Protocol:

PET scans were performed on 12-14-week-old Lewis male rats. Prior to imaging, the animals were anesthetized by isoflurane inhalation. After a transmission scan of the area of interest had been acquired (used to perform attenuation correction of the emission data), the radioligand [$^{11}$C]DTBZ was administered (0.5-1.0 µCi/gm) in saline as a bolus injection via the penile vein. PET scans of the animals were acquired dynamically to 90 minutes post-injection on a Concorde microPET-R4 (CTI Molecular Imaging (Knoxville, Tenn.)). The scanner provided a 100×80 mm field of view with a reconstructed resolution of 2.25 mm in the central 40 mm of the field of view.

At thirty minutes post injection of [$^{11}$C]DTBZ, animals received a second injection via the penile vein of cold analog. PET data were processed using an attenuation correction matrix obtained by transmission scans and images were reconstructed using Fourier rebinning, followed by two-dimensional, filtered back projection using microPET manager software (CTI Molecular Imaging (Knoxville, Tenn.)).

Example 2

Glucose Tolerance in Adult Lewis Rats is Improved by TBZ

Older heavier Lewis rats display glucose intolerance relative to younger animals during an IPGTT (Natalucci, et al. 2003; Wang, et al. 1997). To explore the role of VMAT2 in insulin secretion, and to better demonstrate the possible value of VMAT2 as a potential therapeutic target, older male Lewis rats (300-500 grams, >11 weeks of age) were selected for IPGTT testing. For this study only rats with vehicle-alone AUC IPGTT values greater than 10 g/dL×min were used. Doses of tetrabenazine (TBZ) were selected that were approximately three to ten fold higher than the equivalent doses currently used in humans to treat movement disorders (Kenney and Jankovic 2006). Following TBZ administration (about 1 hour), but before glucose challenge, no reproducible differences were found in the baseline fasting glucose concentrations of control animals (data not shown). Following TBZ treatment and glucose challenge, however, a significant change was found in the shape of the glucose disposition curve during IPGTT (FIG. 1A).

Comparison of the areas under the curve during IPGTT revealed that TBZ reduced the glucose excursion by approximately 35% at 2.25 µg/gm body weight (FIG. 1A). This dose represented a maxima of the glucose tolerance enhancing effects of TBZ; at doses lower than 0.3 mg/Kg, the effects of TBZ became undetectable by this assay, and at doses higher than 5.0 mg/Kg, the AUC IPGTT became increasingly variable, often surpassing that of control levels. Chronic administration of TBZ at approximately 0.1 mg/Kg body weight for five days suppressed the AUC IPGTT in a fashion similar to the single high dose (data not shown).

Example 3

TBZ Depletes Total Pancreatic Dopamine and L-DOPA Reverses Effects of TBZ

Figure 2:
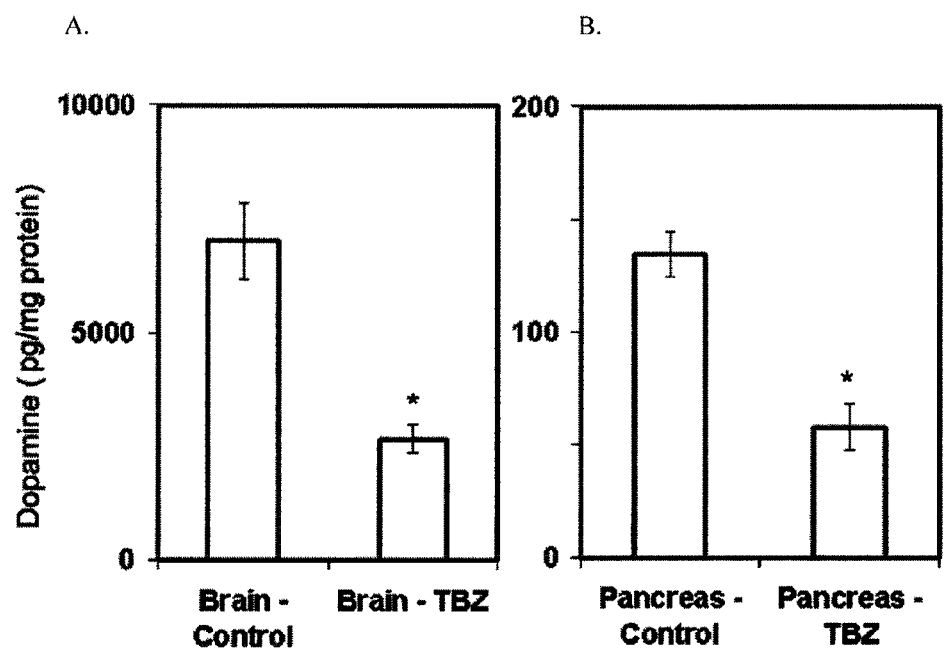
FIG. 2 demonstrates that TBZ reduces the dopamine content of brain (A) and pancreas (B) tissue. Tetrabenazine at 1.5 mg/Kg body weight was administered intravenously (i.v.) to Lewis rats. One hour later, the animals were euthanized and the brains and pancreata harvested and extracted in buffer. The dopamine concentration in the extract was determined by ELISA and normalized to the total protein content. The error bars represent the S.E.M. from measurements of three TBZ treated and three control Lewis rats. An asterisk represents a significant difference ($p<0.05$) from control.

Dopamine is a well-known substrate of VMAT2-mediated vesicular transport (Howell, et al., 1994) and one of the main reported actions of TBZ is the depletion of dopamine in brain tissue (Kenney and Jankovic 2006). To explore the possible role of dopamine in mediating the in vivo glucose tolerance enhancing effects of TBZ, the effects of TBZ on the concentration of dopamine were examined in both the pancreas and the brain. One hour after injection of TBZ, the dopamine content of both tissues was significantly reduced (FIG. 2). Because islets compose only about 2% of the pancreas, the marked effects of TBZ on total pancreatic dopamine content likely reflects dopamine depletion in non islet pancreatic tissue elements as well. The IPGTT experiments were repeated with TBZ. In these experiments, however, L-DOPA, the metabolic precursor of dopamine or a vehicle control, was administered one hour following TBZ and concurrent with glucose.

The results revealed that L-DOPA (6.0 mg/Kg, via I.P. injection) was able to reverse the effects of TBZ, increasing the AUC IPGTT to slightly below control levels.

Example 4

TBZ Enhances In Vivo Glucose-Dependent Insulin Secretion

Figure 3:
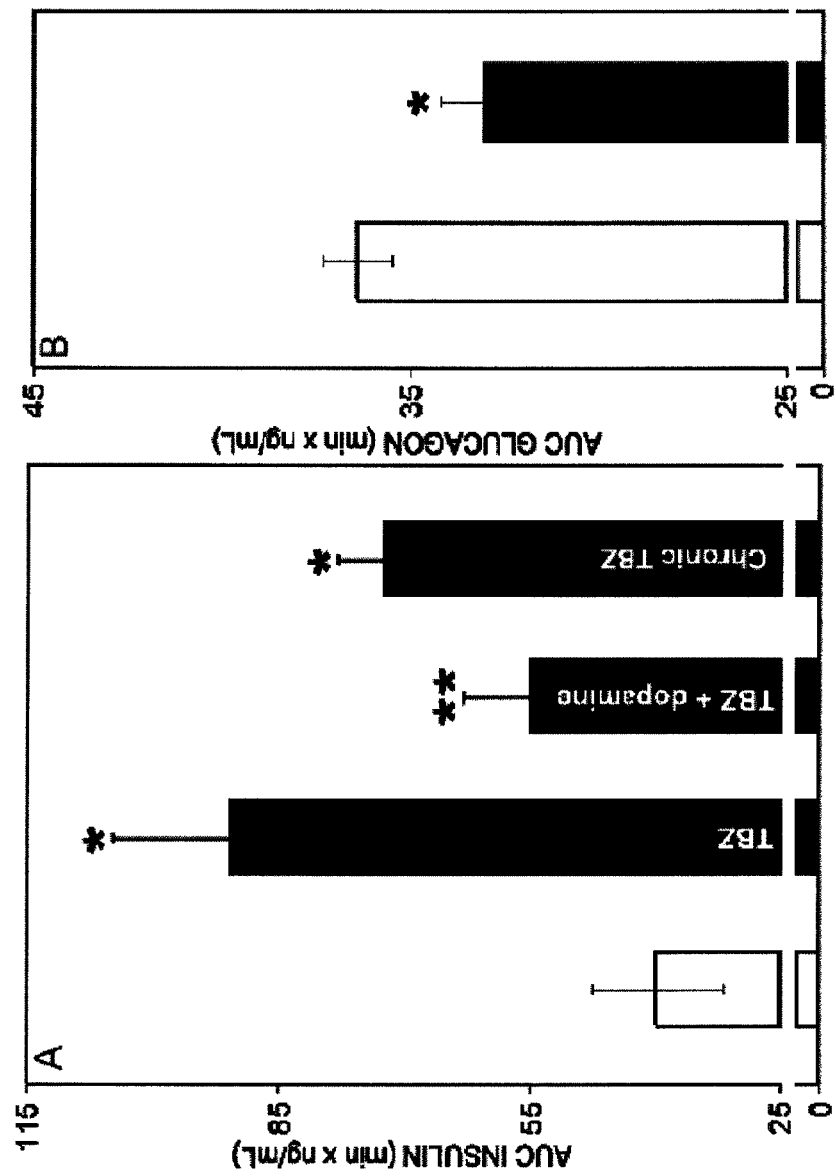
FIG. 3 demonstrates that tetrabenazine alters glucose stimulated insulin and glucagon secretion in vivo. Plasma insulin (FIGS. 3A and 3C) and glucagon concentrations (FIGS. 3B and 3D) were measured during IPGTT of Lewis rats (>11 weeks old) (n=6) treated with vehicle alone (open columns and circles). One week later, a second IPGTT was performed with TBZ (2.25 mg/Kg body weight) (filled columns and circles), TBZ (2.25 mg/Kg body weight) plus dopamine (6.0 mg/Kg), or following five daily injections TBZ (0.3 mg/Kg body weight). An asterisk represents a significant difference ($p<0.05$) from control.
Figure 3:
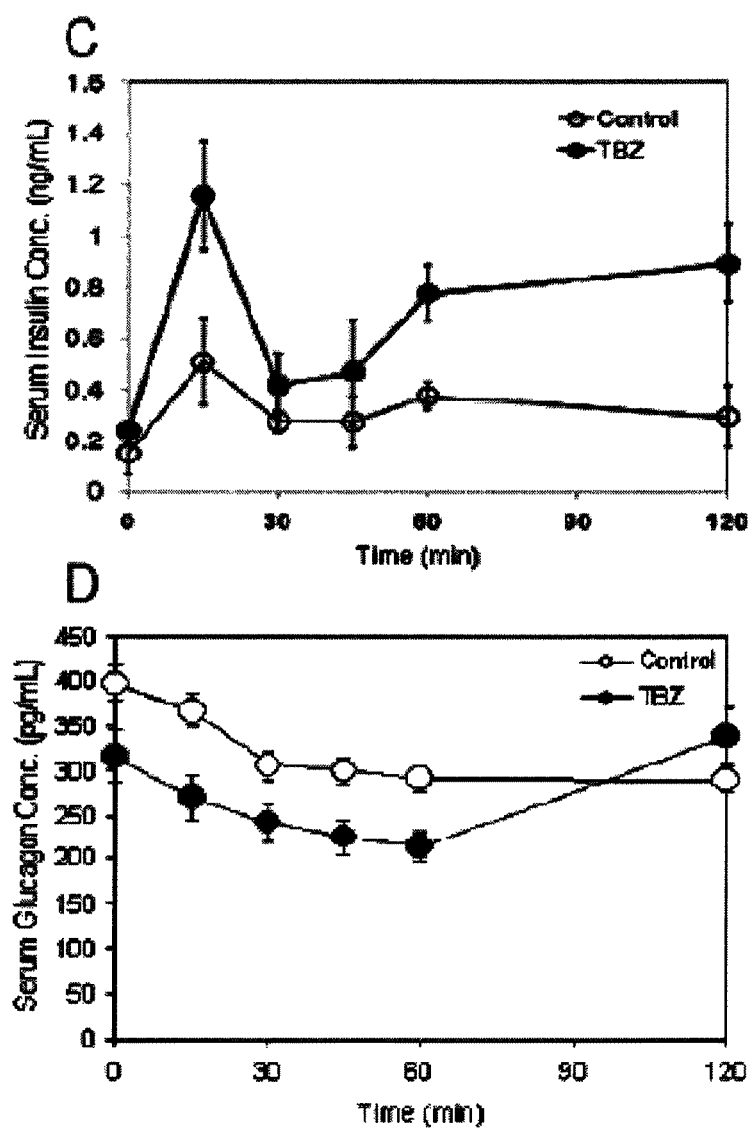

The hypothesis that the smaller glucose excursions in IPGTT seen after administration of TBZ were due to increased insulin concentrations in the plasma following glucose stimulation was tested. Blood glucose, plasma insulin and glucagon concentrations in blood samples obtained during IPGTT were measured (FIG. 3A-3D). Both area under the curve (AUC) insulin and glucagon (GCG) measurements were changed by administration of TBZ. Plasma insulin amounts were significantly greater following a single dose of TBZ or chronic low doses of TBZ (0.1 mg/Kg body weight/day×5 days) and glucose challenge relative to the vehicle-treated controls. In addition, dopamine, given via i.v. injection at the same time as glucose, partially blocked the insulin enhancing effects of TBZ (FIG. 3A). The AUC plasma glucagon measurements were lower relative to controls following i.v. TBZ administration and glucose challenge (FIGS. 3B and 3D). The change in AUC glucagon however was less than the change in AUC insulin. In STZ treated rats which maintained glucose dependant insulin secretion, TBZ (1.5 mg/Kg) increased the AUC insulin measurement by approximately 50%-80% and decreased AUC IPGTT (data not shown).

Example 5

Figure 4:
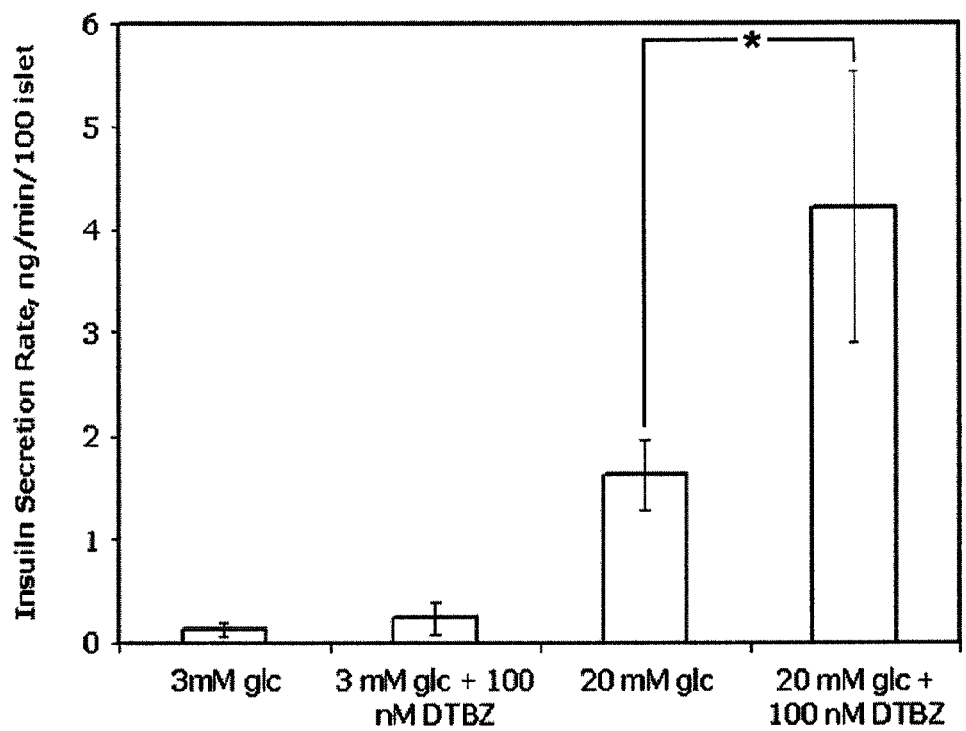
FIG. 4 demonstrates that DTBZ enhances glucose stimulated insulin secretion in rat islets ex vivo. Hand picked purified islets were cultured in high or low glucose containing media with and without DTBZ. Serial insulin concentration measurements in the supernatant were performed and the means and S.E.M. calculated. An asterisk represents a significant difference ($p<0.05$) from control.

TBZ Enhances In Vitro Glucose-Dependent Insulin Secretion in Purified Rat Islets Because VMAT2 is located throughout the CNS and glucose homeostasis is regulated by the autonomic nervous system, a critical question was whether TBZ was acting locally in islets. Whether the VMAT2 antagonist dihydrotetrabenazine (DTBZ), the direct and active metabolite of TBZ, could enhance insulin secretion in purified rat islets tested in vivo was tested. The islets were incubated in high and low glucose media with and without DTBZ. Insulin secretion increased ten fold in response to glucose, and was significantly further enhanced by DTBZ two to three fold (p<0.05) (FIG. 4). At low glucose, an increase in insulin secretion mediated by DTBZ was not statistically significant.

Example 6

DTBZ does not Act Through DPP-IV Inhibition

DTBZ structurally belongs to a class of quinolizine alkaloids. Recently, certain quinolizine alkaloids have been shown to increase insulin levels through inhibiting dipeptidyl peptidase VI (DDP-IV), a serine protease that cleaves the insulin-stimulating incretin hormone glucagon-like peptide-1 (Lubbers et al, 2007). To examine whether DPP-IV plays a role in DTBZ's insulin enhancement, DTBZ's effect on DDP-IV in vitro was tested. DTBZ had no effect on DPP-IV at concentrations up to 10 µM (data not shown).

Example 7

VMAT2 is Expressed in Rodent Islets and Beta Cells

Figure 5:
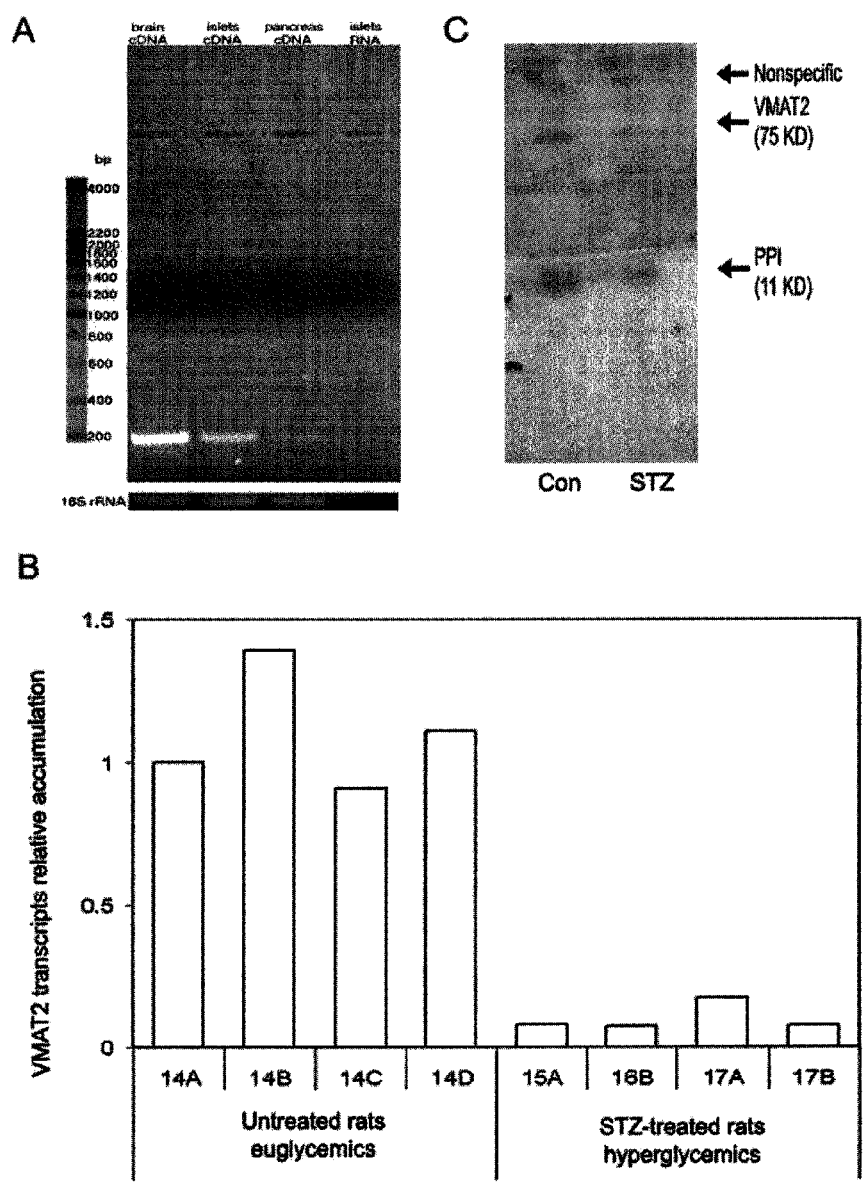
FIG. 5 shows VMAT2 mRNA and protein in islets and pancreas of control and streptozotocin treated Lewis rats.

As opposed to VMAT2 expressed by human beta cells (Anlauf et al. 2003), the presence of VMAT2 in rodent islets cannot be detected by immunohistochemistry using currently available commercial antisera. To demonstrate that VMAT2 is associated with rat islets, the following series of experiments were performed. First, total RNA was prepared from brain, purified islets obtained from rodent pancreata, and total pancreas. Total RNA was then reverse transcribed and amplified with specific primers for rat VMAT2. A 175 bp cDNA fragment of the length and structure expected from the published sequence of rat VMAT2 (Erickson, et al. 1992) was amplified and sequenced (FIG. 5A). Total RNA from brain was used as a positive control (FIG. 5A, lane 1).

Quantitation of specific VMAT2 transcripts in islets total RNA versus complete pancreas total RNA showed that VMAT2-specific RNA was enriched >10 fold in islets relative to total pancreas (FIG. 5A, lane 2 versus lane 3). In the absence of the reverse transcription reaction, no PCR product was found (FIG. 5A, lane 4). Within the pancreas, insulin producing beta cells uniquely express the GLUT2 transporter. The toxin STZ selectively targets and destroys beta cells following transport by GLUT2 (Szkudelski 2001; Elsner, et al., 2000). To demonstrate that VMAT2 is associated with beta cells of the endocrine pancreas, the selective beta cell toxicity of STZ was used. Total RNA from pancreata obtained from four control rats and four STZ-induced diabetic rats was prepared. Quantitation of VMAT2 message by real time PCR showed that treatment with STZ significantly reduced the amount of VMAT2 in diabetic pancreata relative to control pancreata 84 to 92% (99.9% CI) (FIG. 5B). When protein lysates were prepared from pancreata obtained from control rats and STZ-induced diabetic rats, separated by SDS-PAGE, transferred to membranes and then probed with VMAT2 antibodies, the loss of VMAT2 protein, as well as preproinsulin protein, following STZ treatment was visible by the loss of the western blotting signal (FIG. 5C).

Example 8

Model for the Role of VMAT2 in Islet Function

Several previous studies have demonstrated a link between insulin secretion and dopamine. For example, treatment of Parkinson's patients with dopamine precursor, L-DOPA, reduces insulin secretion in glucose tolerance tests (Rosati, et al. 1976). In rodent experiments, i.v. administration of L-DOPA inhibits glucose-stimulated insulin secretion (Ericson, et al. 1977; Zern, et al. 1980). In culture, analogues of dopamine inhibit glucose-stimulated insulin release by purified islets (Arneric, et al. 1984). Most recently, Rubi et al. (Rubi et al. 2005) demonstrated that mouse beta cells (INS-1 E cells), as well as purified rat and human islets, express the dopamine D2 receptor. In these cells and tissues, the D2 receptor was shown to colocalize with insulin in secretory granules in a pattern similar to the colocalization of VMAT2 and insulin (Anlauf et al. 2003). Both dopamine and the D2-like receptor agonist, quinpirole, inhibited glucose-stimulated insulin secretion when tested in primary rat beta cells, and rat, mouse and human pancreatic islets.

Together with the studies of Rubi et al. (Rubi et al. 2005) and others (Brodoff and Kagan 1972) the following model for the role of VMAT2 in islet function can be proposed. Dopamine produced locally in the beta cell cytoplasm is normally transported and stored in insulin-containing vesicles. In the presence of TBZ, the vesicular storage of dopamine declines. Under normal glucose stimulated insulin secretion, dopamine is co-released with insulin and acts either in an autocrine or paracrine fashion to limit glucose-stimulated insulin secretion by other local beta cells. In the presence of TBZ, this negative feedback loop is not present and less dopamine is released with insulin and other local beta cells remain uninhibited by dopamine. The studies disclosed herein focused on dopamine as the most likely intermediate mediator of the effects of TBZ, although it is not ruled out that other monoamines, such as serotonin, etc., also play a role in the observed in vivo effects of TBZ.

Example 9

Repeated Low Doses of TBZ May Also be Active in Reducing Glucose Excursions

Currently, arginine pulse stimulation of insulin secretion is a gold standard measurement for evaluating functional beta cell mass. Preliminary studies by the inventors with TBZ suggest that more detailed glucose clamp and insulin secretion measurements should be performed, and the inventors continue to evaluate whether inhibition of VMAT2 might further improve the hyperglycemic clamp technique applied to evaluating beta cell mass. To date, the inventors have found that repeated low doses of TBZ may also be active in reducing glucose excursions. In other studies the inventors have found some evidence from PET pharmacokinietic studies that DTBZ may accumulate in the pancreas. Together these data suggest that chronic low doses of TBZ may also result in antagonism of VMAT2.

Example 10

Synthesis of Novel VMAT2 Antagonists

Figure 6:
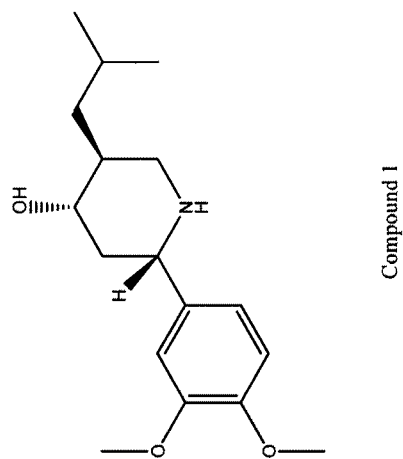
FIG. 6 shows the structures of TBZ, DTBZ and compound 1.
Figure 6:
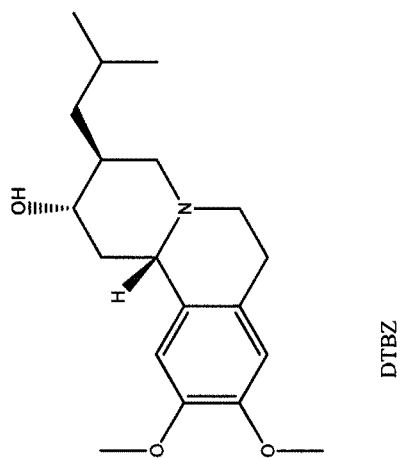
Figure 6:
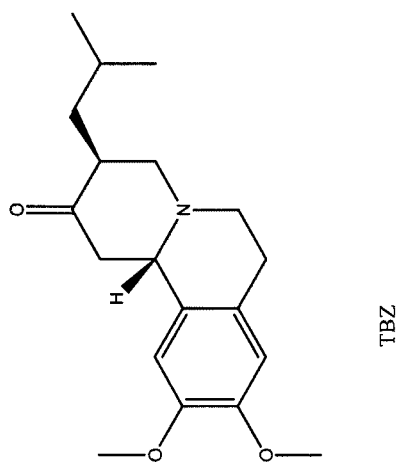
Figure 9:
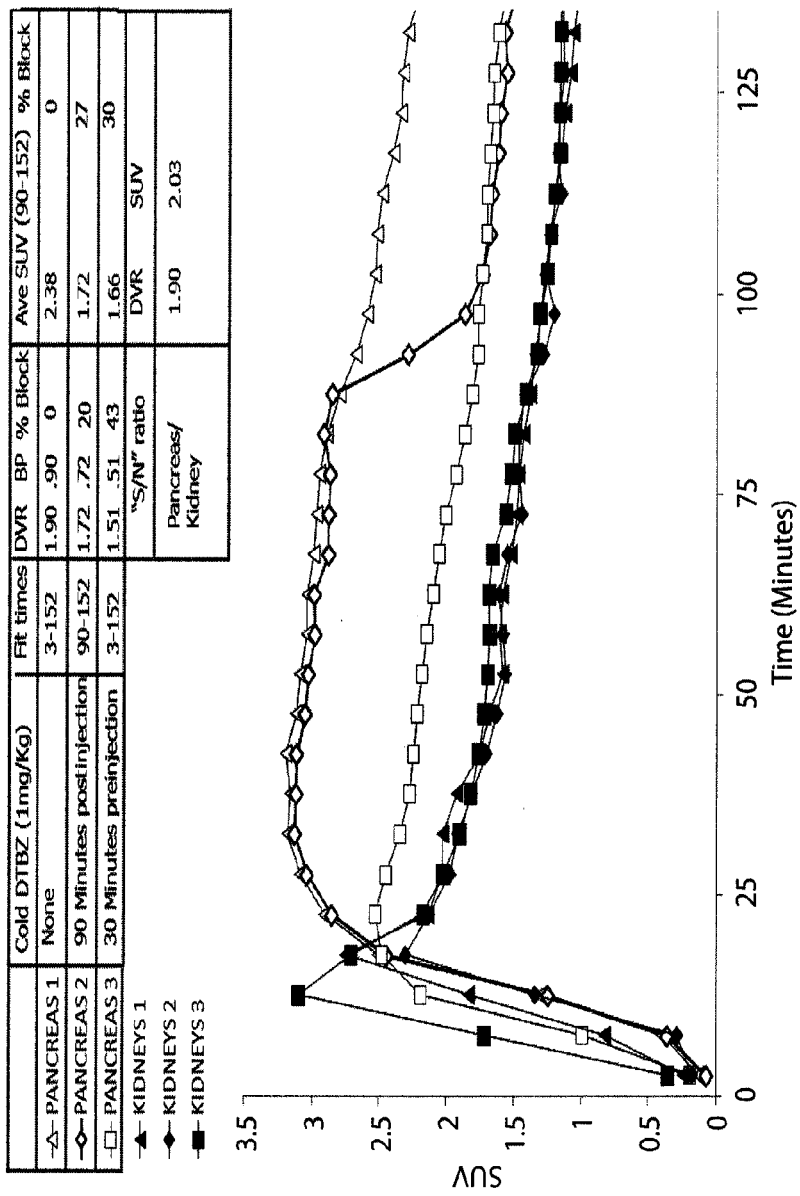
FIG. 9 is a graph showing the quantitation of [$^{11}$C]DTBZ uptake in Lewis rat pancreas.

In an effort to generate novel VMAT2 antagonists, compound 1 (shown in FIG. 6), a simplified analog of DTBZ, was synthesized. As shown in FIG. 9, veratraldehyde (compound 2) was treated with ammonium acetate at 50° C. for 3 hours and converted into β-amino acid (compound 3) by condensation with malonic acid at 80° C. for 24 hours. Protection with Boc anhydride at room temperature for 24 hours and subsequent condensation with potassium malonate methyl ester for 2 days at room temperature led to a β-keto ester (compound 4). Alkylation with isobutyl bromide in the presence of potassium carbonate for 3 hours at reflux temperature afforded a mixture of compound 5 and compound 6 in moderate yield.

After removal of the Boc group, the mixture was treated with sodium bicarbonate in methanol for 24 hours at room temperature to yield the cyclized products, compound 7 and compound 8 quantitatively. Compound 9 was obtained from reduction of compound 7 with sodium borohydride at room temperature for 1 hour and then further converted to compound 1 and its diastereoisomers with lithium aluminum hydride.

Example 11

Glucose Tolerance Tests of Novel Compounds

Figure 7:
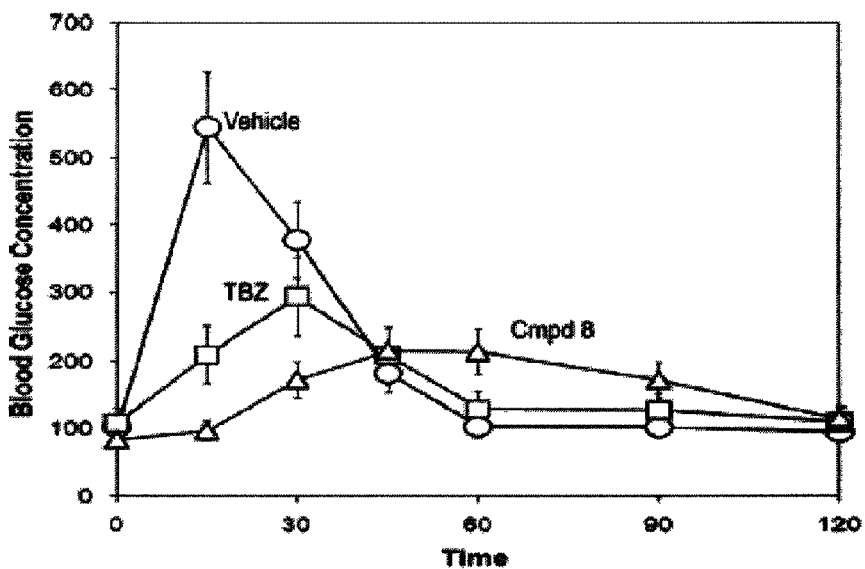
FIG. 7 shows the results of the glucose tolerance tests of novel hypoglycemic compounds. Six hours fasted Lewis rats were administered various compounds intravenously (30 minutes, 2 mg/kg) followed by intraperitoneal glucose injection (0 minute, 2 g/kg), and blood glucose levels were monitored for 120 minutes.
Figure 7:
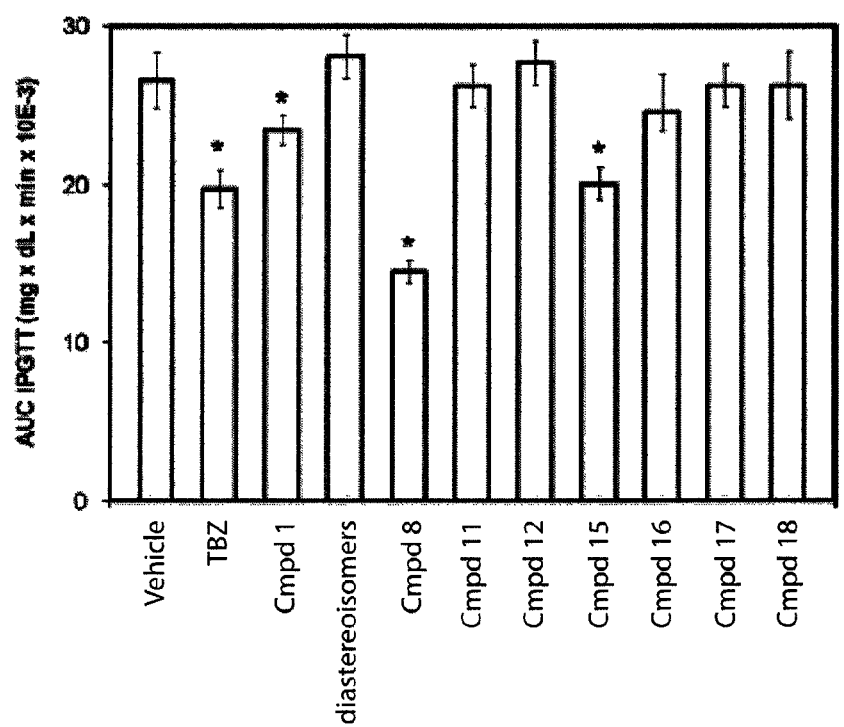

Racemic compound 1 and its diastereoisomers were evaluated for their ability to improve glucose tolerance by IPGTTs in rats. These new analogs were less potent than TBZ possibly due to diminished affinity for VMAT2 (FIG. 7). Accordingly, these analogs were not further pursued.

During random screens of intermediates generated in the course of the synthesis of compound 1, it was found that compound 8, a novel dihydropyridone resulted from the competing O- versus C-alkylation of enolic β-keto ester compound 4 followed by cyclization, showed potent hypoglycemic effect. As illustrated in FIG. 7, compound 8 decreased the AUC IPGTT by 45% at the dose of 2 mg/kg compared to 26% for TBZ.

Example 12

Synthesis and Characterization of Analogs of Compound 8

Prompted by this surprising result, analogs of compound 8 were designed and synthesized.

Figure 10:
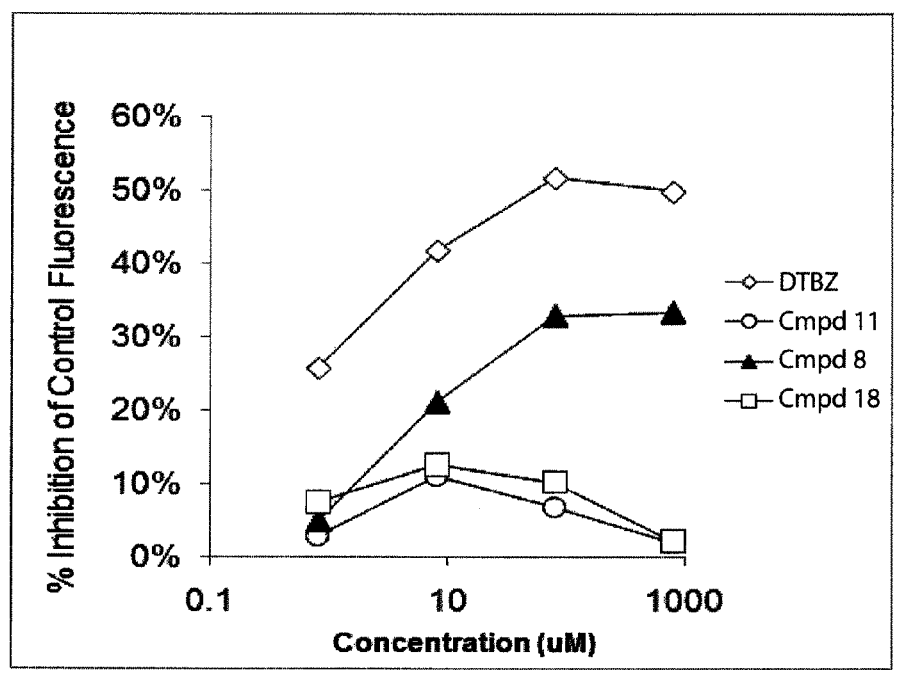
FIG. 10 is a graph showing % inhibition of control fluorescence in a high throughput screen according to the present invention.
Figure 11:
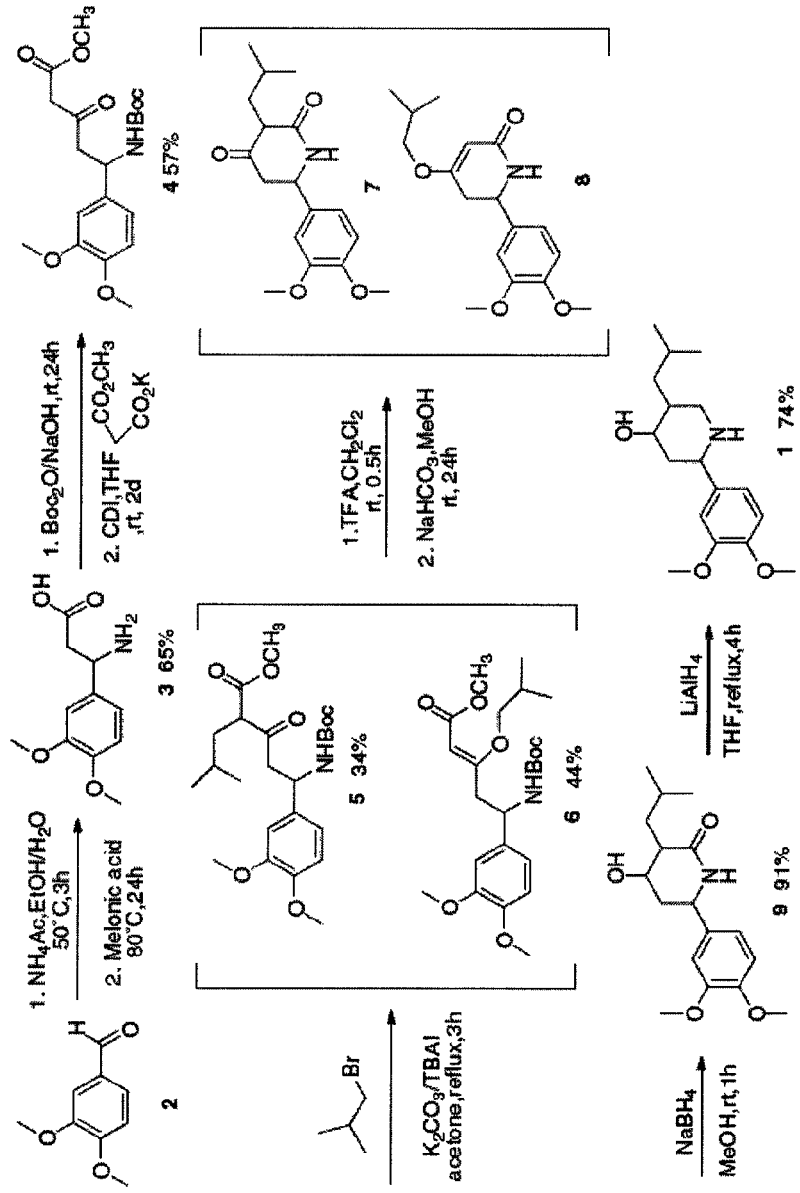
FIG. 11 shows the synthetic scheme of compound 1. The first number under a structure sets forth the compound number. For example, "1" indicates compound 1.
Figure 12:
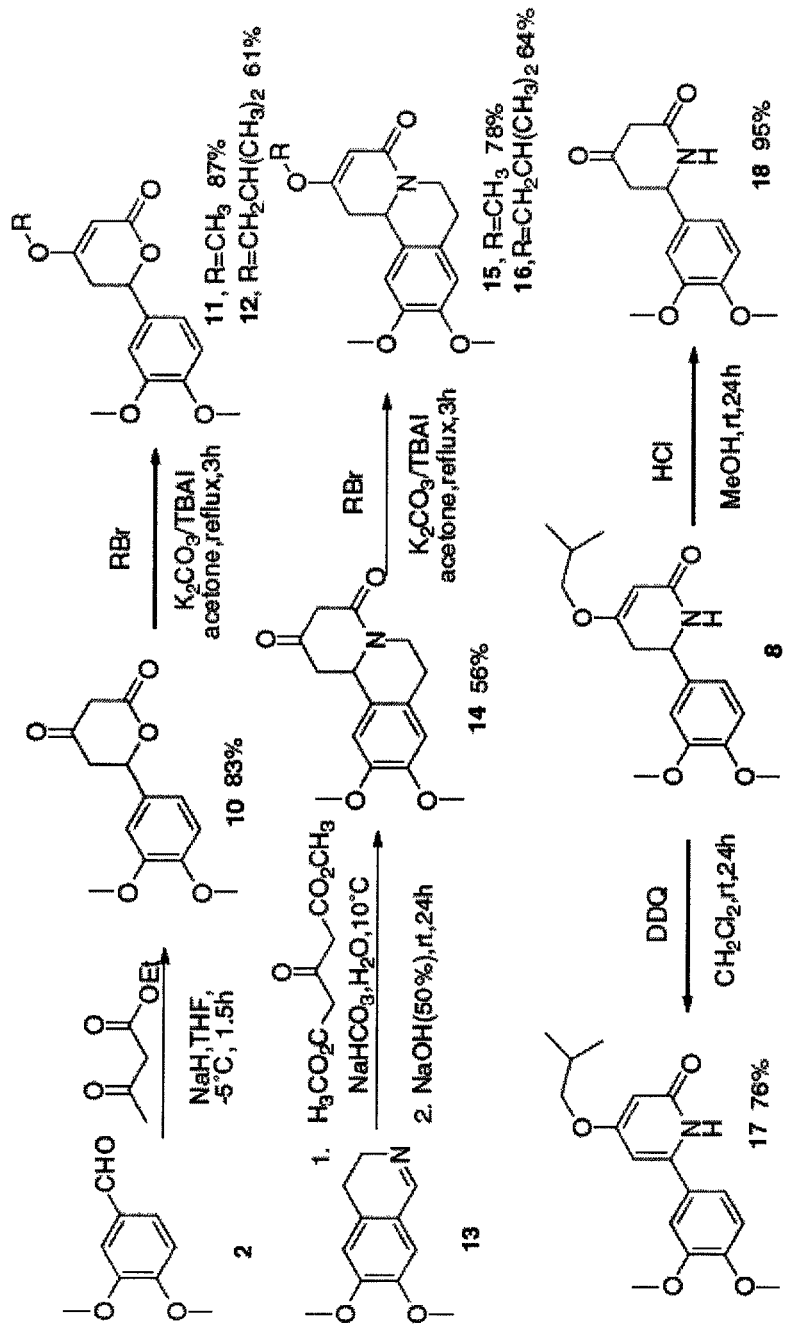
FIG. 12 shows the synthetic schemes of analogs of compound 8. The first number under a structure sets forth the compound number.

As outlined in FIG. 10, veratraldehyde (compound 2) was first condensed with ethyl acetoacetate at −5° C. for 1.5 hours, and spontaneous cyclization yielded lactone, compound 10. Using potassium carbonate as the base, O-alkylation of compound 10 with methyl bromide or isobutyl bromide provided compound 11 and compound 12.

Similarly, compounds 15 and 16 were prepared from dihydroisoquinoline, compound 13, via condensation with dimethyl 1,3-acetonedicarboxylate followed by cyclization and alkylation.

Aromatization induced by 2,3-dichloro-5,6-dicyanobenzoquinone (DDQ) and acidic hydrolysis of compound 8 afforded compound 17 and compound 18, respectively. Using conventional methods, other analogs of compound 8 may be readily synthesized and tested for activity using, e.g., the methods disclosed herein.

Analogs prepared as above were tested for their hypoglycemic activities in rats using the IPGTT protocol. Interestingly, the hypoglycemic effects of these compounds were only seen following glucose stimulation. Results shown in FIG. 7 demonstrated that the dihydropyridone scaffold in compound 8 is essential for the hypoglycemic activity. Replacement with dihydropyrone (compound 11 and compound 12), oxidation, or hydrolysis of 8 (compound 17, compound 18) resulted in the total loss of activities.

Interestingly, the rigid derivatives, compound 15 and compound 16 were active but less potent, in opposition to the structure-activity relationship trend seen in compound 1 and DTBZ.

Analytical data for compound 8 are as follows: $^1$H NMR (300 MHz, CDCl$_3$) δ 6.90-6.85 (m, 2H), 6.84 (s, 1H), 5.45 (br, 1H), 5.07 (s, 1H), 4.69-4.63 (dd, 1H), 3.87 (s, 3H), 3.86 (s, 3H), 3.64-3.60 (m, 2H), 2.71-2.47 (m, 2H), 2.02-1.96 (m, 1H), 0.96-0.93 (dd, 6H); $^{13}$C NMR (75 MHz, CD$_3$OD) δ 170.0, 168.9, 149.4, 149.1, 133.5, 119.0, 111.4, 109.3, 93.8, 75.1, 56.3, 56.2, 55.0, 37.3, 28.1, 19.5, 19.4; ESI-MS (M$^+$+H): 306.3.

Analytical data for compound 15 are as follows: $^1$H NMR (300 MHz, CDCl$_3$) δ 6.58 (s, 1H), 6.54 (s, 1H), 5.15 (s, 1H), 4.71-4.65 (m, 2H), 3.80 (s, 3H), 3.79 (s, 3H), 3.67 (s, 3H), 2.81-2.60 (m, 4H), 2.48-2.37 (m, 1H); $^{13}$C NMR (75 MHz, CD$_3$OD) δ 168.3, 167.4, 148.0 (2C), 127.4, 127.3, 111.3, 108.6, 94.6, 56.3, 56.2, 56.0, 54.1, 38.4, 37.2, 29.4; ESI-MS (M$^+$+H): 290.1.

Example 13

Compound 8 Binds to VMAT2

To test whether the strong hypoglycemic effect of compound 8 is conferred by binding to VMAT2 in beta cells, a PET study in rats was performed. The animals were treated with radiolabeled DTBZ, and the uptake of [$^{11}$C]DTBZ in pancreas was monitored by PET scan in the presence of an excess of compound 8.

Figure 8:
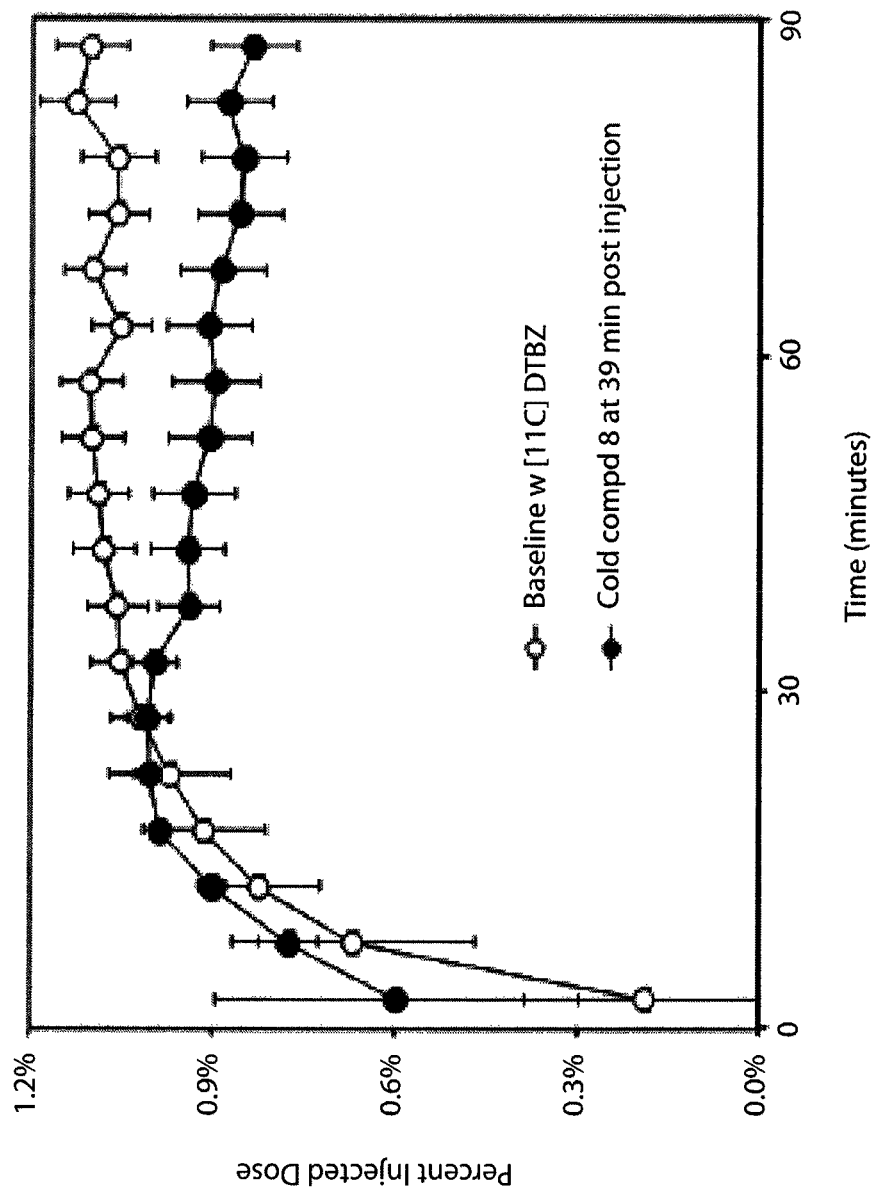
FIG. 8 shows the effect, post-injection, of compound 8 on biodistribution of [$^{11}$C]DTBZ in pancreas. Positron emission tomography (PET) scans were performed on anesthetized 12-14-week-old Lewis male rats injected with radioligand [$^{11}$C]DTBZ (0 minute, 0.5-1.0 μCi/gm body weight, specific activity >2000 mCi/mol) and cold compound 8 (30 minutes, 2 mg/kg). The fraction of radioligand in pancreas relative to the total amount of injected was calculated and plotted versus time after injection. Error bars indicate S.E.M. (n=3). The area under the curve (AUC) from 30 minutes to 90 minutes was calculated by the trapezoidal rule for each experiment. The statistical significance of the difference between the average AUC baseline and AUC compound 8 was $p>0.05$ as calculated by the method of Student.

Contrary to the inventors' original interpretation (Xie et al., 2008), it is now believed that compound 8 does show binding to VMAT2. A comparison of the binding curves for the displacement of [$^{11}$C]DTBZ in the endocrine pancreas by compound 8 (FIG. 8) versus the displacement of [$^{11}$C]DTBZ by authentic cold DTBZ (FIG. 9) suggests that there is at least a weak binding of compound 8 to VMAT2 relative to DTBZ. Alternatively, VMAT2 is known to possess multiple binding sites (Darchen, et al., 1989 and Scherman et al., 1984) and one could hypothesize that compound 8 is binding to a site dissimilar to that used by DTBZ.

An alternative mechanism of action, suggested by the inventors' PET studies and in vivo experiments might be that compound 8 is a competitive inhibitor of DA transport with no D2R action or is a competitive inhibitor of DA transport with D2R antagonist activity. It has been demonstrated that [$^{11}$C] (+)DTBZ binding to VMAT2 is sensitive to changes in vesicular DA storage levels (Tong et al., 2008). If compound 8 is transported by VMAT2 into vesicles, at the expense of DA, this could alter [$^{11}$C] (+)DTBZ binding to VMAT2.

A high throughput (HTP) assay was developed to screen for compounds that interact with, e.g., bind to, VMAT2. The HTP exploits a class of compounds called Fake Fluorescent Neurotransmitters (FFN) that share the following characteristics a) low molecular weight and sufficiently hydrophilic to be water soluble; b) in aqueous buffer (pH 7), the excitation maxima is around 380-406 nm and the emission maxima is around 501 nm; and c) similar Kd for VMAT2 as dopamine. To validate the use of these compounds in beta cell lines (positive for VMAT2) the following set of experiments were performed.

The rat INS 832/13 cell line was selected because it secretes insulin in response to glucose concentrations in the physiological range and can be shown to contain VMAT2 by PCR. INS 832/13 cells were stably transfected with a plasmid containing the human proinsulin gene and after subcloning was found to be responsive to glucose in terms of insulin secretion (Hohmeier et al., 2000). INS cells were grown on cover slips in normal media, then pretreated with and without DTBZ in low glucose media for one hour and then loaded with FFN (GH206). The distribution of fluorescent dye was then examined under a fluorescent microscope. The FFN distributes itself intracellularly in a punctate pattern similar, if not identical, to insulin containing granules of this cell line (data not shown). In addition, it was observed that DTBZ exhibited a block effect on the uptake of FFN (data not shown). For better quantitation of the fluorescent signal, the cells were grown in 46 well plates and the same experiment substantially repeated. Briefly, cells were grown to confluence in complete high glucose media, then incubated for one hour in low glucose media. DTBZ was then added to the wells for one hour, followed with a second one hour incubation with FFN. Wells were then washed and the fluorescent signal (380 exc, 512 emm) measured in a multiwell fluorometer (Synergy HT Multi-Mode Microplate Reader).

The measurements of fluorescence (data not shown) confirmed that DTBZ was able to block uptake of FFN in these cells and suggested that this assay format may be suitable for detecting other compounds that act as competitive inhibitors of DA uptake by VMAT2 as well as antagonists of VMAT2 DA transport.

To test whether this assay was suitable to screen synthetic analogs of TBZ for inhibition of VMAT2 function, compounds 8, 11, and 18 were tested. The results of that assay are shown in FIG. 10. These results suggest that compound 8 is able to block FFN transport into INS vesicles, although its activity on a per mole basis seems less than that of DTBZ.

Example 13

Compound 8 does not Act Through DPP-IV Inhibition

DTBZ and its analogs are structurally similar to a class of quinolizine alkaloids previously shown to inhibit dipeptidyl peptidase IV (DPP-IV) (Lubbers et al, 2007), but compound 8 tested negative against DPP-IV in vitro at concentrations up to 10 µM (data not shown). Therefore, the mechanism underlying the anti-hyperglycemic effect of compound 8 is not through DPP-IV inhibition.

Pending U.S. Provisional Application Ser. No. 61/188,419 filed Aug. 8, 2008 entitled Hypoglycemic Dihydropyridones, International Application No. PCT/US08/03338 entitled Methods and Compositions for Modulating Insulin Secretion and Glucose Metabolism, which was filed on Mar. 12, 2008, U.S. Provisional Application Ser. No. 60/906,623, filed on Mar. 12, 2007, and U.S. Provisional Application Ser. No. 60/932,810, filed May 31, 2007, are incorporated herein by reference in their entireties for all purposes.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

CITED DOCUMENTS

The following documents, including all documents cited above, are incorporated by reference as if recited in full herein:

Adeghate E & Donath T 1991 Dopamine-beta-hydroxylase-positive nerves in normal and transplanted pancreatic tissue in the anterior eye-chamber of rats. *J Chem Neuroanat* 4 223-227.

Ahren B 2000 Autonomic regulation of islet hormone secretion—implications for health and disease. *Diabetologia* 43 393-410.

Ahren B, Jarhult J & Lundquist I 1981 Influence of the sympatho-adrenal system and somatostatin on the secretion of insulin in the rat. *J Physiol* 312 563-575.

Ahren B & Lundquist I 1985 Effects of L-dopa-induced dopamine accumulation on 45Ca2+ efflux and insulin secretion in isolated rat islets. *Pharmacology* 30 71-82.

Aleyassine H & Gardiner R J 1975 Dual action of antidepressant drugs (MAO inhibitors) on insulin release. *Endocrinology* 96 702-710.

Anlauf M, Eissele R, Schafer M K, Eiden L E, Arnold R, Pauser U, Kloppel G & Weihe E 2003 Expression of the two isoforms of the vesicular monoamine transporter (VMAT1 and VMAT2) in the endocrine pancreas and pancreatic endocrine tumors. *J Histochem Cytochem* 51 1027-1040.

Arneric S P, Chow S A, Long J P & Fischer L J 1984 Inhibition of insulin release from rat pancreatic islets by drugs that are analogues of dopamine. *Diabetes* 33 888-893.

Barker C J, Leibiger I B, Leibiger B & Berggren P O 2002 Phosphorylated inositol compounds in beta—cell stimulus—response coupling. *Am J Physiol Endocrinol Metab* 283 E1113-1122.

Borelli M I & Gagliardino J J 2001 Possible modulatory effect of endogenous islet catecholamines on insulin secretion. *BMC Endocr Disord* 1 1.

Borelli M I, Rubio M, Garcia M E, Flores L E & Gagliardino J J 2003 Tyrosine hydroxylase activity in the endocrine pancreas: changes induced by short-term dietary manipulation. *BMC Endocr Disord* 3 2.

Borelli M I, Villar M J, Orezzoli A & Gagliardino J J 1997 Presence of DOPA decarboxylase and its localisation in adult rat pancreatic islet cells. *Diabetes Metab* 23 161-163.

Brice N L, Varadi A, Ashcroft S J & Molnar E 2002 Metabotropic glutamate and GABA(B) receptors contribute to the modulation of glucose-stimulated insulin secretion in pancreatic beta cells. *Diabetologia* 45 242-252.

Brodoff B N & Kagan A 1972 Biogenic-Amines and Diabetes in Sand Rat. *Hormone and Metabolic Research* 4 310-311.

Brunicardi F C, Shavelle D M & Andersen D K 1995 Neural regulation of the endocrine pancreas. *Int J Pancreatol* 18 177-195.

Cegrell L 1968 The occurrence of biogenic monoamines in the mammalian endocrine pancreas. *Acta Physiol Scand Suppl* 314 1-60.

Darchen, F., D. Scherman, and J. P. Henry. 1989. Reserpine binding to chromaffin granules suggests the existence of two conformations of the monoamine transporter. *Biochemistry* 28:1692-1697.

Duttaroy A, Zimliki C L, Gautam D, Cui Y, Mears D & Wess J 2004 Muscarinic stimulation of pancreatic insulin and glucagon release is abolished in m3 muscarinic acetylcholine receptor-deficient mice. *Diabetes* 53 1714-1720.

Eiden L E, Schafer M K, Weihe E & Schutz B 2004 The vesicular amine transporter family (SLC18): amine/proton antiporters required for vesicular accumulation and regulated exocyto tic secretion of monoamines and acetylcholine. *Pflugers Arch* 447 636-640.

Ekholm R, Ericson L E & Lundquist I 1971 Monoamines in the pancreatic islets of the mouse. Subcellular localization of 5-hydroxytryptamine by electron microscopic autoradiography. *Diabetologia* 7 339-348.

El-Mansoury A M & Morgan N G 1998 Activation of protein kinase C modulates alpha2-adrenergic signalling in rat pancreatic islets. *Cell Signal* 10 637-643.

Elsner M, Guldbakke B, Tiedge M, Munday R & Lenzen S 2000 Relative importance of transport and alkylation for pancreatic beta-cell toxicity of streptozotocin. *Diabetologia* 43 1528-1533.

Erickson J D, Eiden L E & Hoffman B J 1992 Expression cloning of a reserpine-sensitive vesicular monoamine transporter. *Proc Natl Acad Sci USA* 89 10993-10997.

Erickson J D, Schafer M K, Bonner T I, Eiden L E & Weihe E 1996 Distinct pharmacological properties and distribution in neurons and endocrine cells of two isoforms of the human vesicular monoamine transporter. *Proc Natl Acad Sci USA* 93 5166-5171.

Ericson L E, Hakanson R & Lundquist I 1977 Accumulation of dopamine in mouse pancreatic B-cells following injection of L-DOPA. Localization to secretory granules and inhibition of insulin secretion. *Diabetologia* 13 117-124.

Feldman J M & Chapman B 1975a Characterization of pancreatic islet monoamine oxidase. *Metabolism* 24 581-588.

Feldman J M & Chapman B 1975b Monoamine oxidase inhibitors: nature of their interaction with rabbit pancreatic islets to alter insulin secretion. *Diabetologia* 11 487-494.

Goland R et al. 2009 $^{11}$C-dihydrotetrabenazine PET of the pancreas in subjects with long-standing type 1 diabetes and in healthy controls. *J. Nucl Med.* 50 382-9.

Hansen S E & Hedeskov C J 1977 Simultaneous determination of the content of serotonin, dopamine, noradrenaline and adrenaline in pancreatic islets isolated from fed and starved mice. *Acta Endocrinol (Copenh)* 86 820-832.

Hayashi M, Yamada H, Uehara S, Morimoto R, Muroyama A, Yatsushiro S, Takeda J, Yamamoto A & Moriyama Y 2003 Secretory granule-mediated co-secretion of L-glutamate and glucagon triggers glutamatergic signal transmission in islets of Langerhans. *J Biol Chem* 278 1966-1974.

Henquin J C 2000 Triggering and amplifying pathways of regulation of insulin secretion by glucose. *Diabetes* 49 1751-1760.

Hohmeier, H. E., H. Mulder, G. Chen, R. Henkel-Riegeri, M. Prentki, and C. B. Newgard. 2000. Isolation of INS-1-derived cell lines with robust ATP-sensitive K+ channel-dependent and -independent glucose-stimulated insulin secretion. *Diabetes* 49:424-430.

Howell M, Shirvan A, Stern-Bach Y, Steiner-Mordoch S, Strasser J E, Dean G E & Schuldiner S 1994 Cloning and functional expression of a tetrabenazine sensitive vesicular monoamine transporter from bovine chromaffin granules. *FEBS Lett* 338 16-22.

Iturriza F C & Thibault J 1993 Immunohistochemical investigation of tyrosine-hydroxylase in the islets of Langerhans of adult mice, rats and guinea pigs. *Neuroendocrinology* 57 476-480.

Kenney C & Jankovic J 2006 Tetrabenazine in the treatment of hyperkinetic movement disorders. *Expert Rev Neurother* 6 7-17.

Lane J D, Smith J E, Shea P A & McBride W J 1976 Neurochemical changes following the administration of depleters of biogenic monoamines. *Life Sci* 19 1663-1667.

Livak K J & Schmittgen T D 2001 Analysis of relative gene expression data using real-time quantitative PCR and the 2(-Delta Delta C(T)) Method. *Methods* 25 402-408.

Lubbers A, Bohringer M, Gobbi L, Hennig M, Hunziker D, Kuhn B, Loffler B, Mattei P, Narquizian R, Peters J, Ruff Y, Wessel H P & Wyss P 2007 1,3-Disubstituted 4-aminopiperidines as useful tools in the optimization of the 2-aminobenzo[a]quinolizinedipeptidyl peptidase IV inhibitors. *Biorg Med Chem Lett* 17 2966-2970.

Lundquist I, Ahren B, Hansson C & Hakanson R 1989 Monoamines in pancreatic islets of guinea pig, hamster, rat, and mouse determined by high performance liquid chromatography. *Pancreas* 4 662-667.

Maffei A, Liu Z, Witkowski P, Moschella F, Del Pozzo G, Liu E, Herold K, Winchester R J, Hardy M A & Harris P E 2004 Identification of tissue-restricted transcripts in human islets. *Endocrinology* 145 4513-4521.

Murthy, R.; Harris, P. E.; Simpson, N.; Van Heertum, R.; Leibel, R.; Mann, J. J.; Parsey, R. Eur. J. Nucl. Med. Mol. Imaging. 2008, 35(4), 790.

Natalucci S, Ruggeri P, Cogo C E, Picchio V, Brunori A & Burattini R 2003 Age-related analysis of glucose metabolism in spontaneously hypertensive and normotensive rats. *Exp Physiol* 88 399-404.

Niswender C M, Willis B S, Wallen A, Sweet I R, Jetton T L, Thompson B R, Wu C, Lange A J & McKnight G S 2005 Cre recombinase-dependent expression of a constitutively active mutant allele of the catalytic subunit of protein kinase A. *Genesis* 43 109-119.

Pettibone D J, Totaro J A & Pflueger A B 1984 Tetrabenazine-induced depletion of brain monoamines: characterization and interaction with selected antidepressants. *Eur J Pharmacol* 102 425-430.

Rosati G, Maioli M, Aiello I, Farris A & Agnetti V 1976 Effects of long-term L-dopa therapy on carbohydrate metabolism in patients with Parkinson's disease. *Eur Neurol* 14 229-239.

Rubi B, Ljubicic S, Pournourmohammadi S, Carobbio S, Armanet M, Bartley C & Maechler P 2005 Dopamine D2-like receptors are expressed in pancreatic beta cells and mediate inhibition of insulin secretion. *J Biol Chem* 280 36824-36832.

Scherman D 1986 Dihydrotetrabenazine binding and monoamine uptake in mouse brain regions. *J Neurochem* 47 331-339.

Scherman, D.; Henry, J. P. 1984 Reserpine binding to bovine chromaffin granule membranes. Characterization and comparison with dihydrotetrabenazine binding. *Mol. Pharmacol.*, 25 113-122.

Scherman D, Jaudon P & Henry J P 1983 Characterization of the monoamine carrier of chromaffin granule membrane by binding of [2-3H]dihydrotetrabenazine. *Proc Natl Acad Sci USA* 80 584-588.

Shankar E, Santhosh K T & Paulose C S 2006 Dopaminergic regulation of glucose-induced insulin secretion through dopamine D2 receptors in the pancreatic islets in vitro. *IUBMB Life* 58 157-163.

Souza F, Freeby M, Hultman K, Simpson N, Herron A, Witkowsky P, Liu E, Maffei A & Harris P E 2006 Current progress in non-invasive imaging of beta cell mass of the endocrine pancreas. *Curr Med Chem* 13 2761-2773.

Souza, F.; Simpson, N.; Raffo, A.; Saxena, C.; Maffei, A.; Hardy, M.; Kibourn, M.; Goland, R.; Leibel, R.; Mann, J. J.; Van heertum, R.; Harris, P. E. J. Clin. Invest. 2006, 116(6), 1506.

Storto M, Capobianco L, Battaglia G, Molinaro G, Gradini R, Riozzi B, Di Mambro A, Mitchell K J, Bruno V, Vairetti M P, et al. 2006 Insulin secretion is controlled by mGlu5 metabotropic glutamate receptors. *Mol Pharmacol* 69 1234-1241.

Sweet I R, Cook D L, DeJulio E, Wallen A R, Khalil G, Callis J & Reems J 2004 Regulation of ATP/ADP in pancreatic islets. *Diabetes* 53 401-409.

Sweet I R & Gilbert M 2006 Contribution of calcium influx in mediating glucose-stimulated oxygen consumption in pancreatic islets. *Diabetes* 55 3509-3519.

Szkudelski T 2001 The mechanism of alloxan and streptozotocin action in B cells of the rat pancreas. *Physiol Res* 50 537-546.

Tong, J., A. A. Wilson, I. Boileau, S. Houle, and S. J. Kish. 2008. Dopamine modulating drugs influence striatal (+)-[11C]DTBZ binding in rats: VMAT2 binding is sensitive to changes in vesicular dopamine concentration. *Synapse* 62:873-876.

Varoqui H & Erickson J D 1997 Vesicular neurotransmitter transporters. Potential sites for the regulation of synaptic function. *Mol Neurobiol* 15 165-191.

Wang Y, Perfetti R, Greig N H, Holloway H W, DeOre K A, Montrose-Rafizadeh C, Elahi D & Egan J M 1997 Glucagon-like peptide-1 can reverse the age-related decline in glucose tolerance in rats. *J Clin Invest* 99 2883-2889.

Weksler-Zangen S, Yagil C, Zangen D H, Ornoy A, Jacob H J & Yagil Y 2001 The newly inbred cohen diabetic rat: a nonobese normolipidemic genetic model of diet-induced type 2 diabetes expressing sex differences. *Diabetes* 50 2521-2529.

Wilson J P, Downs R W, Jr., Feldman J M & Lebovitz H E 1974 Beta cell monoamines: further evidence for their role in modulating insulin secretion. *Am J Physiol* 227 305-312.

Xie, Y., A. Raffo, M. Ichise, S. Deng, P. E. Harris, and D. W. Landry. 2008. Novel hypoglycemic dihydropyridones serendipitously discovered from O- versus C-alkylation in the synthesis of VMAT2 antagonists. *Bioorg Med Chem Lett* 18:5111-5114.

Zern R T, Bird J L & Feldman J M 1980 Effect of increased pancreatic islet norepinephrine, dopamine and serotonin concentration on insulin secretion in the golden hamster. *Diabetologia* 18 341-346.

Zimmet, P. Z.; Alberti, K. G. M. M.; Shaw, J. Nature 2001, 414, 782.

Zheng, G.; Dwoskin, L. P.; Crooks, P. A. AAPS J. 2006, 8(4), 689.

---

What is claimed is:

1. A compound of formula II:

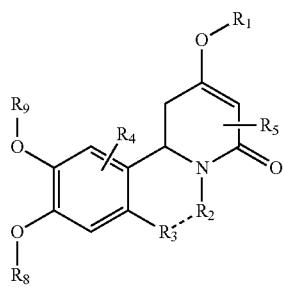

wherein $R_1$, $R_2$, $R_3$, $R_8$ and $R_9$ are independently selected from the group consisting of H, halogen, $C_1$-$C_8$alkyl, $C_1$-$C_8$alkenyl, and $C_1$-$C_8$alkynyl;

$R_4$ and $R_5$, which are attached to one or more positions of at least one carbon atom of the respective rings, are independently selected from the group consisting of H, halogen, hydroxyl, $C_{1-8}$alkyl, $C_{1-8}$alkenyl, $C_{1-8}$alkynyl, and $C_{1-8}$alkoxy; and --- is an optional bond, wherein the optional bond is not present wherein for every occurrence of the C1-C8alkyl, C1-C8alkenyl, or C1-C8alkynyl is an unsubstituted C1-C8alkyl, an unsubstituted C1-C8alkenyl, or an unsubstituted C1-C8alkynyl;

or an enantiomer, optical isomer, diastereomer, N-oxide, crystalline form, hydrate, or pharmaceutically acceptable salt thereof.

2. The compound according to claim 1, wherein the compound has formula III:

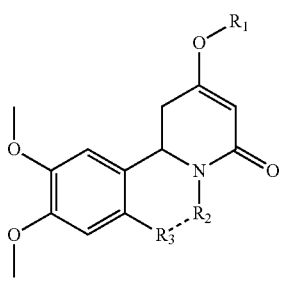

wherein $R_1$, $R_2$, and $R_3$ are independently selected from the group consisting of H, $C_1$-$C_8$alkyl, $C_1$-$C_8$alkenyl, and $C_1$-$C_8$alkynyl; and --- is an optional bond, wherein the optional bond is not present;

or an enantiomer, optical isomer, diastereomer, N-oxide, crystalline form, hydrate, or pharmaceutically acceptable salt thereof.

3. The compound according to claim 2, wherein $R_1$ is selected from the group consisting of H, $C_1$-$C_8$alkyl, $C_1$-$C_8$alkenyl, and $C_1$-$C_8$alkynyl; and $R_2$ and $R_3$ are selected from the group consisting of H and $C_1$alkyl.

4. A compound of formula IV:

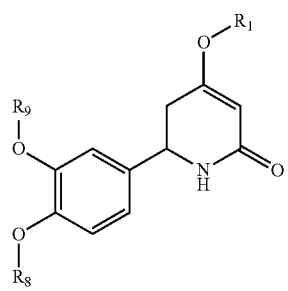

wherein $R_1$, $R_8$, and $R_9$ are independently selected from the group consisting of H, halogen, $C_{1-8}$alkyl, $C_{1-8}$alkenyl, $C_{1-8}$alkynyl, and $C_{1-8}$alkoxy;

or an enantiomer, optical isomer, diastereomer, N-oxide, crystalline form, hydrate, or pharmaceutically acceptable salt thereof.

5. The compound according to claim 4, wherein $R_1$ is —$CH_2$—CH—$(CH_3)_2$.

6. The compound according to claim 4, wherein $R_8$ is methyl.

7. The compound according to claim 4, wherein $R_9$ is methyl.

8. The compound according to claim 4, wherein both $R_8$ and $R_9$ are methyl.

9. The compound according to claim 4, wherein $R_1$ is selected from the group consisting of $C_{1-8}$alkyl, $C_{1-8}$alkenyl, $C_{1-8}$alkynyl, and $C_{1-8}$alkoxy and $R_8$ and $R_9$ are both methyl.

10. The compound according to claim 4, which is compound 8:

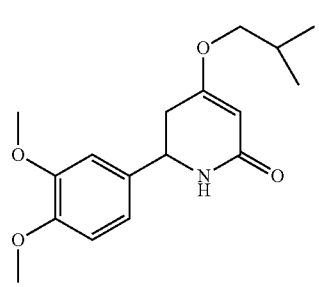

or an enantiomer, optical isomer, diastereomer, N-oxide, crystalline form, hydrate, or pharmaceutically acceptable salt thereof.

11. A compound having the structure (1):
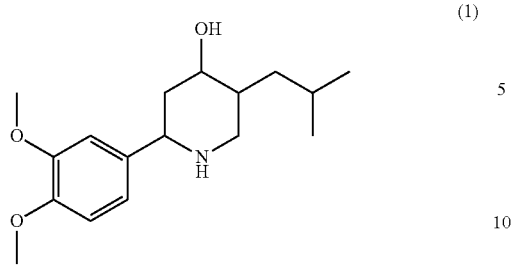
or an enantiomer, optical isomer, diastereomer, N-oxide, crystalline form, hydrate, or pharmaceutically acceptable salt thereof.
12. A pharmaceutical composition comprising a pharmaceutically acceptable carrier and a therapeutically effective amount of a compound according to any one of claim 1, 4 or 10.
* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Synthetic construct

<400> SEQUENCE: 1
cgcaaactga tcctgttcat                                              20

<210> SEQ ID NO 2
<211> LENGTH: 20
<212> TYPE: DNA
<213> ORGANISM: Artificial
<220> FEATURE:
<223> OTHER INFORMATION: Synthetic construct

<400> SEQUENCE: 2
agaagatgct ttcggaggtg                                              20

<210> SEQ ID NO 3
<211> LENGTH: 21
<212> TYPE: DNA
<213> ORGANISM: Artificial
<220> FEATURE:
<223> OTHER INFORMATION: Synthetic construct

<400> SEQUENCE: 3
aacggatttg gccgtatcgg a                                            21

<210> SEQ ID NO 4
<211> LENGTH: 22
<212> TYPE: DNA
<213> ORGANISM: Artificial
<220> FEATURE:
<223> OTHER INFORMATION: Synthetic construct

<400> SEQUENCE: 4
tcgctcctgg aagatggtga tg                                           22

<210> SEQ ID NO 5
<211> LENGTH: 21
<212> TYPE: DNA
<213> ORGANISM: Artificial
<220> FEATURE:
<223> OTHER INFORMATION: Synthetic construct

<400> SEQUENCE: 5
ttsgaacgtc tgccctatca a                                            21

<210> SEQ ID NO 6
<211> LENGTH: 20
```

```
<212> TYPE: DNA
<213> ORGANISM: Artificial
<220> FEATURE:
<223> OTHER INFORMATION: Synthetic construct

<400> SEQUENCE: 6
caattacagg gcctcgaaag                                              20
```